(12) United States Patent
Ohsawa et al.

(10) Patent No.: US 6,551,758 B2
(45) Date of Patent: Apr. 22, 2003

(54) ONIUM SALTS, PHOTOACID GENERATORS, RESIST COMPOSITIONS, AND PATTERNING PROCESS

(75) Inventors: Youichi Ohsawa, Nakakubiki-gun (JP); Jun Watanabe, Nakakubiki-gun (JP); Kazunori Maeda, Nakakubiki-gun (JP)

(73) Assignee: Shin-Etsu Chemical Co. Ltd., Tokyo (JP)

( * ) Notice: Subject to any disclaimer, the term of this patent is extended or adjusted under 35 U.S.C. 154(b) by 0 days.

(21) Appl. No.: 09/983,154

(22) Filed: Oct. 23, 2001

(65) Prior Publication Data

US 2002/0077493 A1 Jun. 20, 2002

(30) Foreign Application Priority Data

Oct. 23, 2000 (JP) ........................................ 2000-322182

(51) Int. Cl.$^7$ ......................... G03F 7/004; C07C 309/29
(52) U.S. Cl. ..................... 430/270.1; 430/326; 430/914; 430/921; 568/30
(58) Field of Search .................... 562/30, 45, 74, 562/78, 83; 549/535; 556/428; 430/270.1, 326, 914, 921

(56) References Cited

U.S. PATENT DOCUMENTS

| | | | |
|---|---|---|---|
| 3,978,024 A | * | 8/1976 | Yano et al. ................. 106/676 |
| 5,492,793 A | | 2/1996 | Breyta et al. |
| 5,558,971 A | | 9/1996 | Urano et al. |
| 5,558,976 A | | 9/1996 | Urano et al. |
| 5,625,020 A | | 4/1997 | Breyta et al. |
| 5,837,420 A | | 11/1998 | Aoai et al. |
| 6,215,021 B1 | * | 4/2001 | Shreeve et al. ................ 562/30 |
| 6,416,928 B1 | * | 7/2002 | Ohsawa et al. .......... 430/270.1 |
| 6,440,634 B1 | * | 8/2002 | Ohsawa et al. .......... 430/270.1 |

FOREIGN PATENT DOCUMENTS

| | | |
|---|---|---|
| JP | 6148889 A | 5/1994 |
| JP | 6199770 A | 7/1994 |
| JP | 6266112 A | 9/1994 |
| JP | 8-123032 A | 5/1996 |
| JP | 11072921 A | 8/1997 |
| JP | 9244234 A | 9/1997 |
| JP | 9258435 A | 10/1997 |

OTHER PUBLICATIONS

CA: 85:32566 abs of Eur J Med Chem Chim Ther by Esteve et al 11(1) pp 43–8 1976.*

* cited by examiner

Primary Examiner—Jean F. Vollano
(74) Attorney, Agent, or Firm—Millen, White, Zelano & Branigan, P.C.

(57) ABSTRACT

Onium salts of arylsulfonyloxybenzenesulfonate anions with iodonium or sulfonium cations are novel. A chemically amplified resist composition comprising the onium salt as a photoacid generator is suited for microfabrication, especially by deep UV lithography because of many advantages including improved resolution, improved focal latitude, minimized line width variation or shape degradation even on long-term PED, minimized debris after coating, development and peeling, and improved pattern profile after development.

12 Claims, No Drawings

ONIUM SALTS, PHOTOACID GENERATORS, RESIST COMPOSITIONS, AND PATTERNING PROCESS

This invention relates to novel onium salts, photoacid generators for resist compositions, resist compositions comprising the photoacid generators, and a patterning process using the same. The resist compositions, especially chemical amplification type resist compositions are sensitive to such radiation as UV, deep UV, electron beams, x-rays, excimer laser beams, γ-rays, and synchrotron radiation and suitable for the microfabrication of integrated circuits.

BACKGROUND OF THE INVENTION

While a number of efforts are currently being made to achieve a finer pattern rule in the drive for higher integration and operating speeds in LSI devices, deep-ultraviolet lithography is thought to hold particular promise as the next generation in microfabrication technology.

One technology that has attracted a good deal of attention recently utilizes as the deep UV light source a high-intensity KrF excimer laser, especially an ArF excimer laser featuring a shorter wavelength. There is a desire to have a microfabrication technique of finer definition by combining exposure light of shorter wavelength with a resist material having a higher resolution.

In this regard, the recently developed, acid-catalyzed, chemical amplification type resist materials are expected to comply with the deep UV lithography because of their many advantages including high sensitivity, resolution and dry etching resistance. The chemical amplification type resist materials include positive working materials that leave the unexposed areas with the exposed areas removed and negative working materials that leave the exposed areas with the unexposed areas removed.

In chemical amplification type, positive working, resist compositions to be developed with alkaline developers, an alkali-soluble phenol or a resin and/or compound in which carboxylic acid is partially or entirely protected with acid-labile protective groups (acid labile groups) is catalytically decomposed by an acid which is generated upon exposure, to thereby generate the phenol or carboxylic acid in the exposed area which is removed by an alkaline developer. Also, in similar negative working resist compositions, an alkali-soluble phenol or a resin and/or compound having carboxylic acid and a compound (crosslinking agent) capable of bonding or crosslinking the resin or compound under the action of an acid are crosslinked with an acid which is generated upon exposure whereby the exposed area is converted to be insoluble in an alkaline developer and the unexposed area is removed by the alkaline developer.

On use of the chemical amplification type, positive working, resist compositions, a resist film is formed by dissolving a resin having acid labile groups as a binder and a compound capable of generating an acid upon exposure to radiation (to be referred to as photoacid generator) in a solvent, applying the resist solution onto a substrate by a variety of methods, and evaporating off the solvent optionally by heating. The resist film is then exposed to radiation, for example, deep UV through a mask of a predetermined pattern. This is optionally followed by post-exposure baking (PEB) for promoting acid-catalyzed reaction. The exposed resist film is developed with an aqueous alkaline developer for removing the exposed area of the resist film, obtaining a positive pattern profile. The substrate is then etched by any desired technique. Finally the remaining resist film is removed by dissolution in a remover solution or ashing, leaving the substrate having the desired pattern profile.

The chemical amplification type, positive working, resist compositions adapted for KrF excimer lasers generally use a phenolic resin, for example, polyhydroxystyrene in which some or all of the hydrogen atoms of phenolic hydroxyl groups are protected with acid labile protective groups. Onium salts such as iodonium salts and sulfonium salts, bissulfonyldiazomethane compounds, and N-sulfonyloxyimide compounds are typically used as the photoacid generator. If necessary, there are added additives, for example, a dissolution inhibiting or promoting compound in the form of a carboxylic acid and/or phenol derivative having a molecular weight of up to 3,000 in which some or all of the hydrogen atoms of carboxylic acid and/or phenolic hydroxyl groups are protected with acid labile groups, a carboxylic acid compound for improving dissolution characteristics, a basic compound for improving contrast, and a surfactant for improving coating characteristics.

Onium salts as shown below are advantageously used as the photoacid generator in chemical amplification type resist compositions, especially chemical amplification type, positive working, resist compositions adapted for KrF excimer lasers because they provide a high sensitivity and resolution and are free from storage instability as found with the N-sulfonyloxyimide photoacid generators.

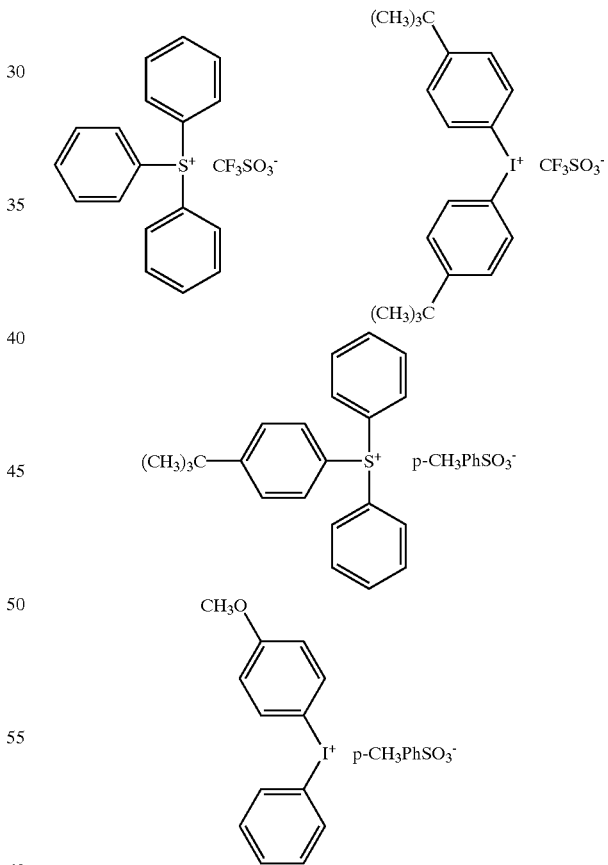

Since a finer pattern size is required, even the use of such photoacid generators gives rise to many problems including low resolution, low environmental stability, and the formation of insoluble or difficultly soluble foreign matter upon development with an alkaline developer or removal of the resist with a solvent.

Of these problems, improvements in resolution are made by introducing into a resin acid labile groups which are more prone to scission by an acid, or adding a basic compound, or modifying processing conditions.

It is known from JP-A 8-123032 to use two or more photoacid generators in a resist material. JP-A 11-72921 discloses the use of a radiation-sensitive acid generator comprising in admixture a compound which generates a sulfonic acid having at least three fluorine atoms upon exposure to radiation and a compound which generates a fluorine atom-free sulfonic acid upon exposure to radiation, thereby improving resolution without inviting nano-edge roughness and film surface roughening. However, we empirically found that these resist compositions are unsatisfactory in resolution and in the effect of eliminating the foreign matter on the pattern upon development.

For the purpose of improving the resolution upon microfabrication, JP-A 6-148889 discloses a positive photosensitive composition comprising a polyfunctional enol ether compound and an alkali-soluble resin as typified by polyhydroxystyrene, which are thermally crosslinked on a substrate, followed by exposure to radiation and PEB to provide a desired pattern. JP-A 6-266112 discloses a photosensitive resist composition comprising a photosensitive acid generator and a polymer composed of hydroxystyrene and an acrylate and/or methacrylate. These compositions are unsatisfactory in resolution and pattern profile. Substantial sliming upon post-exposure delay (PED) is also a problem.

The environmental stability is generally divided into two categories. One environmental stability is related to the deactivation of a photo-generated acid by an air-borne base above the resist film or a base beneath the resist film and on the substrate. This phenomenon is often seen when a photoacid generator capable of generating an acid having a high acid strength is used. It is expected that this problem is solved by introducing into the resin acid labile groups which are more prone to scission by acid or by lowering or weakening the acid strength of the photo-generated acid. The other environmental stability is that when the period from exposure to post-exposure baking (PEB) is prolonged, which is known as post-exposure delay (PED), the photo-generated acid diffuses in the resist film so that acid deactivation may occur when the acid labile groups are less susceptible to scission and acid decomposition may take place when the acid labile groups are susceptible to scission, often inviting a change of the pattern profile in either case. For example, this invites a sliming of the line width in the unexposed area in the case of chemical amplification type, positive working, resist compositions having acid labile groups, typically acetal groups.

As mentioned above, for achieving a high resolution, the resin should have introduced therein acid labile groups which are more prone to scission, and the photoacid generator should desirably generate a less diffusible acid. The less diffusible acids under investigation are alkylsulfonic acids such as 10-camphorsulfonic acid. The alkylsulfonic acids, however, are weak in acid strength as compared with the conventionally used fluorinated alkylsulfonic acids and arylsulfonic acids, and such low acid strength must be compensated for by the quantity of acid. In order that a more quantity of acid be generated, the exposure time must be increased, often leading to poor productivity.

Addressing this problem, JP-A 6-199770, 9-244234 and 9-258435 disclose resist compositions using photoacid generators in the form of arylsulfonic acids having an alkyl, carbonyl or carboxylate group introduced therein.

However, we empirically found that the direct introduction of a carbonyl or carboxylate group into a benzene ring is effective for suppressing the diffusion of the generated acid, but undesirably increases the light absorption near 248 nm of the photoacid generator and that the introduction of an alkyl group can undesirably leave foreign matter upon development.

With respect to the foreign matter left upon alkali development and/or removal of the resist film with a solvent, a variety of factors including photo-decomposed products of the photoacid generator, non-decomposed compound (that is the photoacid generator as such) and-low soluble resin are considered, and none of these factors have been identified responsible. However, the foreign matter is presumably correlated to the solubility or affinity of the photoacid generator in the developer (aqueous solution) or remover solvent and the solubility or affinity thereof in the resin.

The photoacid generator in resist material is required to meet a fully high solubility in (or compatibility with) a resist solvent and a resin, good storage stability, non-toxicity, effective coating, a well-defined pattern profile, PED stability, and no foreign matter left during pattern formation after development and upon resist removal. The conventional photoacid generators, especially those photoacid generators capable of generating alkylsulfonic acids and arylsulfonic acids do not meet all of these requirements.

As the pattern of integrated circuits becomes finer in these days, a higher resolution is, of course, required, and the problems of line width variation by PED and foreign matter after development and resist removal become more serious.

SUMMARY OF THE INVENTION

An object of the invention is to provide a novel onium salt for use in a resist composition, especially of the chemical amplification type, such that the resist composition ensures a high resolution and a well-defined pattern profile after development and minimizes the foreign matter left after development and resist removal. Another object of the invention is to provide a photoacid generator for resist compositions, a resist composition comprising the photoacid generator, and a patterning process using the same.

We have found that by using an onium salt of the general formula (1), especially a sulfonium salt of the general formula (1a) or (1a') or an iodonium salt of the general formula (1b), to be defined below, as the photoacid generator in a resist composition, there are achieved a number of advantages including storage stability, effective coating, minimized line width variation or shape degradation during long-term PED, minimized foreign matter left after coating, development and resist removal, a well-defined pattern profile after development, and a high resolution enough for microfabrication, especially by deep UV lithography.

When the onium salt of formula (1) is used in a chemical amplification type resist composition as the photoacid generator, a resist image featuring a high resolution and a wide range of focal depth is obtainable due to the low diffusing effect of sulfonate anions. At the same time, the degradation of a pattern profile by PED is minimized, and the foreign matter left after alkali development and resist removal is minimized due to the polarity of sulfonium or iodonium salt.

Therefore, the invention provides onium salts, photoacid generators, resist compositions and a patterning process as defined below.

In a first aspect, the invention provides an onium salt of the following general formula (1).

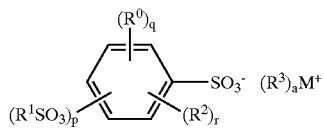

Herein $R^1$ is a substituted or unsubstituted aryl group of 6 to 14 carbon atoms, $R^2$ which may be the same or different is hydrogen or a substituted or unsubstituted, straight, branched or cyclic alkyl group of 1 to 6 carbon atoms, $R^0$ is a hydroxyl, alkoxy, halogen or nitro group, p, q and r each are 1 or 2, $R^3$ which may be the same or different is a substituted or unsubstituted, straight, branched or cyclic alkyl group of 1 to 10 carbon atoms or substituted or unsubstituted aryl group of 6 to 14 carbon atoms, M is a sulfur or iodine atom, and "a" is equal to 3 when M is sulfur and equal to 2 when M is iodine.

A preferred embodiment is a sulfonium salt of the following general formula (1a).

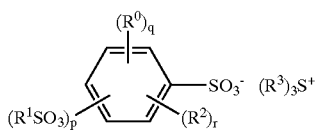

Herein $R^1$, $R^2$, $R^0$, p, q, r and $R^3$ are as defined above.

Another preferred embodiment is a sulfonium salt of the following general formula (1a').

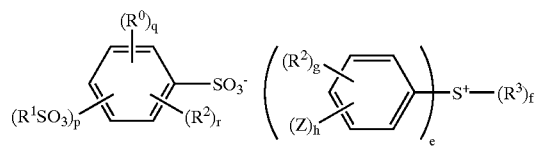

Herein $R^1$, $R^2$, $R^0$, p, q, r and $R^3$ are as defined above, Z is an acid labile group having an oxygen atom attached thereto or $R^2O$— or $(R^2)_2N$—, g is an integer of 0 to 4, h is an integer of 1 to 5, g+h=5, e is an integer of 1 to 3, f is an integer of 0 to 2, and e+f=3.

Preferably, the acid labile group is selected from among tert-butoxy, tert-amyloxy, tert-butoxycarbonyloxy, tert-butoxycarbonylmethyloxy, 1-ethoxyethoxy, tetrahydropyranyloxy, tetrahydrofuranyloxy, trimethylsilyloxy, and 1-ethylcyclopentyloxy groups.

A further preferred embodiment is a iodonium salt of the following general formula (1b).

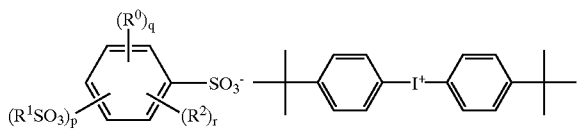

Herein $R^1$, $R^2$, $R^0$, p, q, and r are as defined above.

In a second aspect, the invention provides a photoacid generator for a chemical amplification type resist composition comprising the onium salt defined above.

In a third aspect, the invention provides
a chemical amplification type resist composition comprising (A) a resin which changes its solubility in an alkaline developer under the action of an acid, and (B) the aforementioned photoacid generator which generates an acid upon exposure to radiation; or
a chemical amplification type resist composition comprising (A) a resin which changes its solubility in an alkaline developer under the action of an acid, (B) the aforementioned photoacid generator which generates an acid upon exposure to radiation, and (C) a compound capable of generating an acid upon exposure to radiation, other than component (B). Preferably the resin (A) has such substituent groups having C—O—C linkages that the solubility in an alkaline developer changes as a result of scission of the C—O—C linkages under the action of an acid. The resist composition may further include (D) a basic compound and/or (E) a carboxyl group-containing compound.

In a fourth aspect, the invention provides a process for forming a pattern, comprising the steps of applying the resist composition onto a substrate to form a coating; heat treating the coating and exposing the coating to high energy radiation with a wavelength of up to 300 nm or electron beam through a photo-mask; optionally heat treating the exposed coating, and developing the coating with a developer.

DESCRIPTION OF THE PREFERRED EMBODIMENT

Onium salt

In the first aspect, the invention provides a novel onium salt having a substituted or unsubstituted arylsulfonyloxy-benzenesulfonate anion of the following general formula (1).

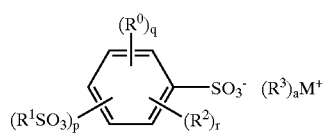

Herein $R^1$ is a substituted or unsubstituted aryl group of 6 to 14 carbon atoms, $R^2$ which may be the same or different is hydrogen or a substituted or unsubstituted, straight, branched or cyclic alkyl group of 1 to 6 carbon atoms, $R^0$ is a hydroxyl group, alkoxy group, halogen atom or nitro group, p, q and r each are 1 or 2, $R^3$ which may be the same or different is a substituted or unsubstituted, straight, branched or cyclic alkyl group of 1 to 10 carbon atoms or substituted or unsubstituted aryl group of 6 to 14 carbon atoms, M is a sulfur or iodine atom, and "a" is equal to 3 when M is sulfur and equal to 2 when M is iodine.

Specifically, the invention provides a novel sulfonium salt having a substituted or unsubstituted arylsulfonyloxy-benzenesulfonate anion of the following general formula (1a) or (1a').

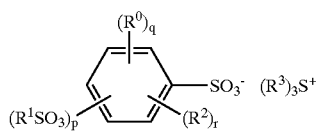

Herein $R^1$, $R^2$, $R^0$, p, q, r and $R^3$ are as defined above.

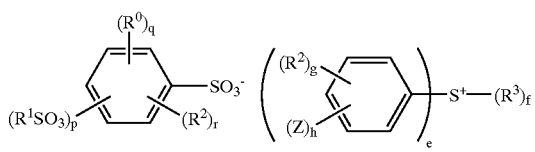

Herein R¹, R², R⁰, p, q, r and R³ are as defined above. Z is an acid labile group having an oxygen atom attached thereto or R²O— or (R²)₂N—, g is an integer of 0 to 4, h is an integer of 1 to 5, g+h=5, e is an integer of 1 to 3, f is an integer of 0 to 2, and e+f=3.

Specifically, the invention also provides a novel iodonium salt having a substituted or unsubstituted arylsulfonyloxybenzenesulfonate anion of the following general formula (1b).

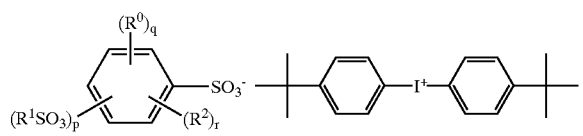

Herein R¹, R², R⁰, p, q and r are as defined above.

In formulae (1), (1a), (1a') and (1b), R¹, which may be the same or different, stands for substituted or unsubstituted aryl groups of 6 to 14 carbon atoms. Illustrative, non-limiting examples include phenyl, 4-methylphenyl, 4-ethylphenyl, 4-methoxyphenyl, 4-tert-butylphenyl, 2,4-dimethylphenyl, 2,4,6-trimethylphenyl, 2,4,6-triisopropylphenyl, 1-naphthyl and 2-naphthyl.

In formulae (1), (1a), (1a') and (1b), R², which may be the same or different, stands for hydrogen or straight, branched or cyclic alkyl groups of 1 to 6 carbon atoms. Illustrative, non-limiting, examples include straight, branched or cyclic alkyl groups such as methyl, ethyl, n-propyl, sec-propyl, n-butyl, sec-butyl, iso-butyl, tert-butyl, n-pentyl, sec-pentyl, cyclopentyl, n-hexyl, and cyclohexyl as well as substituted alkyl groups such as 2-oxopropyl, 2-oxocyclopentyl, 2-oxocyclohexyl, 2-hydroxycyclopentyl and 2-hydroxycyclohexyl.

In formulae (1), (1a), (1a') and (1b), R⁰ stands for a hydroxyl, alkoxy group of 1 to 6 carbon atoms, halogen atom or nitro group. Illustrative, non-limiting examples include hydroxyl groups, straight, branched or cyclic alkoxy groups such as methoxy, ethoxy, n-propoxy, sec-propoxy, n-butoxy, sec-butoxy, iso-butoxy, tert-butoxy, n-pentyloxy, sec-pentyloxy, cyclopentyloxy, n-hexyloxy, and cyclohexyloxy, fluorine, chlorine, bromine and iodine atoms, and nitro groups.

In formulae (1), (1a), (1a') and (1b), R³, which may be the same or different, stands for substituted or unsubstituted, straight, branched or cyclic alkyl groups of 1 to 10 carbon atoms or substituted or unsubstituted aryl groups of 6 to 14 carbon atoms. Illustrative, non-limiting, examples include straight, branched or cyclic alkyl groups such as methyl, ethyl, n-propyl, sec-propyl, n-butyl, sec-butyl, iso-butyl, tert-butyl, n-pentyl, sec-pentyl, cyclopentyl, n-hexyl, and cyclohexyl; substituted alkyl groups such as 2-oxopropyl, 2-oxocyclopentyl, 2-oxocyclohexyl, 2-hydroxycyclopentyl and 2-hydroxycyclohexyl; and aryl groups such as phenyl, 4-methylphenyl, 4-ethylphenyl, 4-methoxyphenyl, 4-tert-butylphenyl, 4-tert-butoxyphenyl, 4-cyclohexylphenyl, 4-cyclohexyloxyphenyl, 2,4-dimethylphenyl, 2,4,6-trimethylphenyl, 2,4,6-triisopropylphenyl, 3,4-bis(tert-butoxy)phenyl, 4-dimethylaminophenyl, 1-naphthyl and 2-naphthyl.

The letters p, q and r each are 1 or 2. In formula (1), M is a sulfur or iodine atom. The letter "a" is equal to 3 when M is sulfur and equal to 2 when M is iodine.

In formula (1a'), Z is an acid labile group having an oxygen atom attached thereto or an alkoxy group: R²O— or a group: (R²)₂N— wherein R² is as defined above. The acid labile group having an oxygen atom attached thereto may be selected from the acid labile groups on high-molecular weight compounds or resins to be described later, though is not limited thereto. Among others, tert-butoxy, tert-amyloxy, tert-butoxycarbonyloxy, tert-butoxycarbonyl-methyloxy, 1-ethoxyethoxy, tetrahydropyranyl, tetrahydro-furanyl, trimethylsilyloxy, and 1-ethylcyclopentyloxy are preferred.

The onium salts of formulae (1), (1a), (1a') and (1b) according to the invention are salts of arylsulfonyloxybenzenesulfonate anions with iodonium or sulfonium cations. Exemplary combinations of anions with cations are given below.

Examples of the sulfonate anion include 3-methoxy-4-(4'-methylphenylsulfonyloxy) benzenesulfonate,
3-methoxy-4-phenylsulfonyloxybenzenesulfonate,
3-methoxy-4-(2',4',6'-trimethylphenylsulfonyloxy) benzenesulfonate,
3-methoxy-4-(2'-naphthylsulfonyloxy)benzenesulfonate,
3-methoxy-4-(1'-naphthylsulfonyloxy)benzenesulfonate,
2-hydroxy-5-(4'-methylphenylsulfonyloxy) benzenesulfonate,
5-hydroxy-2-(4'-methylphenylsulfonyloxy) benzenesulfonate,
3-nitro-4-(4'-methylphenylsulfonyloxy)benzenesulfonate,
3-nitro-4-phenylsulfonyloxybenzenesulfonate,
3-nitro-4-(2',4',6'-trimethylphenylsulfonyloxy) benzenesulfonate,
3-nitro-4-(2'-naphthylsulfonyloxy)benzenesulfonate,
3-nitro-4-(1'-naphthylsulfonyloxy)benzenesulfonate,
3,5-dichloro-2-(4'-methylphenylsulfonyloxy) benzenesulfonate,
3,5-dichloro-2-phenylsulfonyloxybenzenesulfonate,
3,5-dichloro-2-(2',4',6'-trimethylphenylsulfonyloxy) benzenesulfonate,
3,5-dichloro-2-(2'-naphthylsulfonyloxy)benzenesulfonate, and
3,5-dichloro-2-(1'-naphthylsulfonyloxy)benzenesulfonate.

Of these, 3-methoxy-4-(4'-methylphenylsulfonyloxy) benzenesulfonate, 3-methoxy-4-phenylsulfonyloxybenzenesulfonate, 3-nitro-4-(4'-methylphenylsulfonyloxy)benzenesulfonate, and 3,5-dichloro-2-(4'-methylphenylsulfonyloxy)benzenesulfonate are preferred.

Exemplary iodonium cations include diphenyliodonium, bis(4-tert-butylphenyl)iodonium, 4-methoxyphenylphenyliodonium, 4-ethoxyphenylphenyliodonium, and 4-tert-butoxy-phenylphenyliodonium, with the diphenyliodonium and bis(4-tert-butoxyphenyl)iodonium are preferred.

Exemplary sulfonium cations include triphenylsulfonium, 4-hydroxyphenyldiphenylsulfonium, (4-methyl-phenyl) diphenylsulfonium, bis(4-methylphenyl)phenylsulfonium, tris(4-methylphenyl)sulfonium, (4-methoxy-phenyl) diphenylsulfonium, bis(4-methoxyphenyl)phenylsulfonium, tris(4-methoxyphenyl)sulfonium, (4-tert-butyl-phenyl)diphenylsulfonium, bis(4-tert-butylphenyl)phenylsulfonium, tris(4-tert-butylphenyl)sulfonium, (4-tert-butoxyphenyl)diphenylsulfonium, bis(4-tert-butoxyphenyl)-phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-di-tert-butoxyphenyl)diphenylsulfonium, bis(3,4-di-tert-butoxyphenyl)phenylsulfonium, tris(3,4-di-tert-butoxy-phenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 2-naphthyldiphenylsulfonium, dimethyl-2-naphthylsulfonium, 4-hydroxyphenyldimethylsulfonium, 4-methoxyphenyldimethylsulfonium, dimethylphenylsulfonium, diphenylmethylsulfonium, trimethyl-sulfonium, 2-oxocyclohexylcyclohexylmethylsulfonium, 2-oxocyclohexyl-methyl-phenylsulfonium, 2-oxocyclopentyl-methyl-phenylsulfonium, 2-oxocyclopropyl-methyl-phenylsulfonium, and tribenzylsulfonium. Of these, triphenylsulfonium, 4-tert-butoxyphenyldiphenylsulfonium, dimethylphenylsulfonium, and 4-tert-butylphenyldiphenylsulfonium are preferred.

Especially useful onium salts are:

triphenylsulfonium 3-methoxy-4-(4'-methylphenylsulfonyloxy)benzenesulfonate,
4-tert-butoxyphenyldiphenylsulfonium 3-methoxy-4-(4'-methyl-phenylsulfonyloxy)benzenesulfonate,
4-tert-butylphenyldiphenylsulfonium 3-methoxy-4-(4-methyl-phenylsulfonyloxy)benzenesulfonate,
dimethylphenylsulfonium 3-methoxy-4-(4'-methylphenyl-sulfonyloxy)benzenesulfonate,
tris(4-tert-butoxyphenyl)sulfonium 3-methoxy-4-(4'-methyl-phenylsulfonyloxy)benzenesulfonate,
tris(4-tert-butylphenyl)sulfonium 3-methoxy-4-(4'-methyl-phenylsulfonyloxy)benzenesulfonate,
tris(4-methylphenyl)sulfonium 3-methoxy-4-(4'-methylphenyl-sulfonyloxy)benzenesulfonate,
bis(4-tert-butylphenyl)iodonium 3-methoxy-4-(4'-methyl-phenylsulfonyloxy)benzenesulfonate,
diphenyliodonium 3-methoxy-4-(4'-methylphenylsulfonyloxy)-benzenesulfonate,
triphenylsulfonium 3-nitro-4-(4'-methylphenylsulfonyloxy)-benzenesulfonate,
4-tert-butoxyphenyldiphenylsulfonium 3-nitro-4-(4'-methyl-phenylsulfonyloxy)benzenesulfonate,
4-tert-butylphenyldiphenylsulfonium 3-nitro-4-(4'-methyl-phenylsulfonyloxy)benzenesulfonate,
dimethylphenylsulfonium 3-nitro-4-(4'-methylphenylsulfonyl-oxy)benzenesulfonate,
tris(4-tert-butoxyphenyl)sulfonium 3-nitro-4-(4'-methyl-phenylsulfonyloxy)benzenesulfonate,
tris(4-tert-butylphenyl)sulfonium 3-nitro-4-(4'-methyl-phenylsulfonyloxy)benzenesulfonate,
tris(4-methylphenyl)sulfonium 3-nitro-4-(4'-methylphenyl-sulfonyloxy)benzenesulfonate,
bis(4-tert-butylphenyl)iodonium 3-nitro-4-(4'-methylphenyl-sulfonyloxy)benzenesulfonate, and
diphenyliodonium 3-nitro-4-(4'-methylphenylsulfonyloxy)-benzenesulfonate.

The onium salts can be synthesized by the following method although the synthesis method is not limited thereto.

The sulfonyloxybenzenesulfonic acid of the onium salt according to the invention may be obtained by condensing phenol sulfonic acid with a sulfonyl halide or sulfonic anhydride or by sulfonating a phenyl sulfonate.

In condensing phenolsulfonic acid with a sulfonyl halide or sulfonic anhydride, basic conditions must be employed.

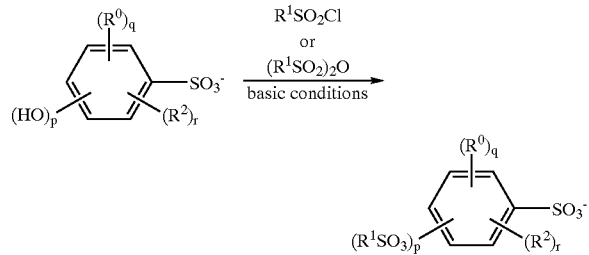

In condensing a phenol with sulfonyl chloride, reaction is also preferably carried out under basic conditions. Sulfonating can be effected by a conventional method using sulfur trioxide, sulfuric acid, chlorosulfonic acid, amidosulfuric acid or the like.

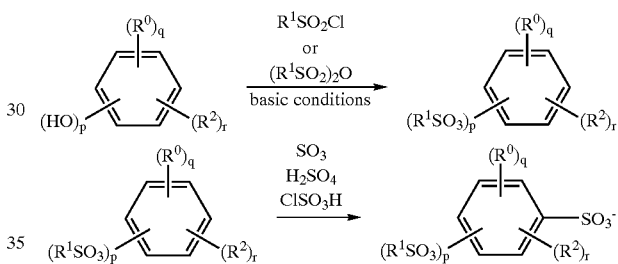

Illustrative, non-limiting examples of the phenolsulfonic acid used herein include 4-hydroxy-3-methoxybenzenesulfonic acid, 2,5-dihydroxybenzenesulfonic acid, 4-hydroxy-3-nitrobenzenesulfonic acid, 3,5-dichloro-2-hydroxybenzenesulfonic acid and alkali metal salts thereof. Illustrative, non-limiting examples of the sulfonyl halide or sulfonic anhydride used herein include benzenesulfonyl chloride, 4-toluenesulfonyl chloride, 4-methoxybenzenesulfonyl chloride, 4-fluorobenzenesulfonyl chloride, 2,4,6-trimethylbenzenesulfonyl chloride, 1-naphthylsulfonyl chloride, 2-naphthylsulfonyl chloride and acid anhydrides of the foregoing sulfonyl chlorides.

The process for the synthesis of corresponding sulfonium and iodonium salts is not critical although the preferred anions are halide ions and alkylsulfonic acids having a lower acid strength than arylsulfonic acids. It is noted that a sulfonium salt having a strong acid such as trifluoromethanesulfonic acid is difficult to effect anion exchange with the above-synthesized sulfonyloxybenzene-sulfonic acid. The sulfonium and iodonium salts can be synthesized according to the teachings of The Chemistry of Sulfonium Group, Part 1, John-Wiley & Sons (1981), Advanced Photochemistry, vol. 17, John-Wiley & Sons (1992), J. Org. Chem., 1988, 53, 5571–5573, JP-A 7-25846, and JP-A 8-311018.

The anion exchange may be effected in an alcoholic solvent such as methanol or ethanol or a two-layer system such as dichloromethane-water.

The onium salts of formula (1), (1a), (1a') or (1b) find best use as the photoacid generator in resist materials, especially chemical amplification type resist materials although the application of the onium salts is not limited thereto. The invention provides resist compositions comprising onium salts of formula (1), (1a), (1a') or (1b) as the photoacid generator.

Resist Composition

The onium salts of formula (1), (1a), (1a') or (1b) are useful as the photoacid generator in chemical amplification type resist compositions. The resist compositions may be either positive or negative working.

The resist compositions of the invention include a variety of embodiments, 1) a chemically amplified positive working resist composition comprising (A) a resin which changes its solubility in an alkaline developer under the action of an acid, (B) an onium salt capable of generating an acid upon exposure to radiation of formula (1), (1a), (1a') or (1b), and (G) an organic solvent;

2) a chemically amplified positive working resist composition of 1) further comprising (C) a photoacid generator capable of generating an acid upon exposure to radiation other than component (B);

3) a chemically amplified positive working resist composition of 1) or 2) further comprising (D) a basic compound;

4) a chemically amplified positive working resist composition of 1) to 3) further comprising (E) an organic acid derivative;

5) a chemically amplified positive working resist composition of 1) to 4) further comprising (F) a compound with a molecular weight of up to 3,000 which changes its solubility in an alkaline developer under the action of an acid;

6) a chemically amplified negative working resist composition comprising (B) an onium salt capable of generating an acid upon exposure to radiation of formula (1), (1a), (1a') or (1b), (H) an alkali-soluble resin, (I) an acid crosslinking agent capable of forming a crosslinked structure under the action of an acid, and (G) an organic solvent;

7) a chemically amplified negative working resist composition of 6) further comprising (C) another photoacid generator;

8) a chemically amplified negative working resist composition of 6) or 7) further comprising (D) a basic compound; and 9) a chemically amplified negative working resist composition of 6), 7) or 8) further comprising (J) an alkali-soluble compound with a molecular weight of up to 2,500; but are not limited thereto.

Moreover, the invention provides a process for forming a pattern, comprising the steps of applying the resist composition defined above onto a substrate to form a coating; heat treating the coating and exposing the coating to high energy radiation with a wavelength of up to 300 nm or electron beam through a photo-mask; optionally heat treating the exposed coating, and developing the coating with a developer.

Now the respective components of the resist composition are described in detail.

Component (G)

Component (G) is an organic solvent. Illustrative, non-limiting, examples include butyl acetate, amyl acetate, cyclohexyl acetate, 3-methoxybutyl acetate, methyl ethyl ketone, methyl amyl ketone, cyclohexanone, cyclopentanone, 3-ethoxyethyl propionate, 3-ethoxymethyl propionate, 3-methoxymethyl propionate, methyl acetoacetate, ethyl acetoacetate, diacetone alcohol, methyl pyruvate, ethyl pyruvate, propylene glycol monomethyl ether, propylene glycol monoethyl ether, propylene glycol monomethyl ether propionate, propylene glycol monoethyl ether propionate, ethylene glycol monomethyl ether, ethylene glycol monoethyl ether, diethylene glycol monomethyl ether, diethylene glycol monoethyl ether, 3-methyl-3-methoxybutanol, N-methyl-pyrrolidone, dimethylsulfoxide, γ-butyrolactone, propylene glycol methyl ether acetate, propylene glycol ethyl ether acetate, propylene glycol propyl ether acetate, methyl lactate, ethyl lactate, propyl lactate, and tetramethylene sulfone. Of these, the propylene glycol alkyl ether acetates and alkyl lactates are especially preferred.

It is noted that the alkyl groups of the propylene glycol alkyl ether acetates are preferably those of 1 to 4 carbon atoms, for example, methyl, ethyl and propyl, with methyl and ethyl being especially preferred. Since the propylene glycol alkyl ether acetates include 1,2- and 1,3-substituted ones, each includes three isomers depending on the combination of substituted positions, which may be used alone or in admixture. It is also noted that the alkyl groups of the alkyl lactates are preferably those of 1 to 4 carbon atoms, for example, methyl, ethyl and propyl, with methyl and ethyl being especially preferred. These solvents may be used alone or in admixture. An exemplary useful solvent mixture is a mixture of a propylene glycol alkyl ether acetate and an alkyl lactate. The mixing ratio of the propylene glycol alkyl ether acetate and the alkyl lactate is not critical although it is preferred to mix 50 to 99 parts by weight of the propylene glycol alkyl ether acetate with 50 to 1 parts by weight of the alkyl lactate. It is more preferred to mix 60 to 95% by weight of the propylene glycol alkyl ether acetate with 40 to 5% by weight of the alkyl lactate. A lower proportion of the propylene glycol alkyl ether acetate would invite a problem of inefficient coating whereas a higher proportion thereof would provide insufficient dissolution and allow for particle and foreign matter formation. A lower proportion of the alkyl lactate would provide insufficient dissolution and cause the problem of many particles and foreign matter whereas a higher proportion thereof would lead to a composition which has a too high viscosity to apply and loses storage stability. The solvent mixture of the propylene glycol alkyl ether acetate and the alkyl lactate may further contain one or more other solvents.

Component (A)

Component (A) is a resin which changes its solubility in an alkaline developer solution under the action of an acid. It is preferably, though not limited thereto, an alkali-soluble resin having phenolic hydroxyl and/or carboxyl groups in which some or all of the phenolic hydroxyl and/or carboxyl groups are protected with acid-labile protective groups represented by C—O—C or C—O—Si linkages.

The alkali-soluble resins having phenolic hydroxyl and/or carboxyl groups include homopolymers and copolymers of p-hydroxystyrene, m-hydroxystyrene, α-methyl-p-hydroxystyrene, 4-hydroxy-2-methylstyrene, 4-hydroxy-3-methylstyrene, methacrylic acid and acrylic acid, and such copolymers having a carboxylic derivative or diphenyl ethylene introduced at their terminus.

Also included are copolymers in which units free of alkali-soluble sites such as styrene, α-methylstyrene, acrylate, methacrylate, hydrogenated hydroxystyrene, maleic anhydride and maleimide are introduced in addition to the above-described units in such a proportion that the solubility in an alkaline developer may not be extremely reduced. Substituents on the acrylates and methacrylates may be any of the substituents which do not undergo acidolysis. Exemplary substituents are straight, branched or cyclic $C_{1-8}$ alkyl groups and aromatic groups such as aryl groups, but not limited thereto.

Examples of the alkali-soluble resins are given below. These polymers may also be used as the material from which the resin (A) which changes its solubility in an alkaline developer under the action of an acid is prepared and as the alkali-soluble resin which serves as component (H) to be described later. Examples include poly(p-hydroxystyrene), poly(m-hydroxystyrene), poly(4-hydroxy-2-methylstyrene), poly(4-hydroxy-3-methylstyrene), poly(α-methyl-p-hydroxystyrene), partially hydrogenated p-hydroxystyrene copolymers, p-hydroxystyrene-α-methyl-p-hydroxystyrene copolymers, p-hydroxystyrene-α-methylstyrene copolymers, p-hydroxystyrene-styrene copolymers, p-hydroxystyrene-m-hydroxystyrene copolymers, p-hydroxystyrene-styrene copolymers, p-hydroxystyrene-acrylic acid copolymers, p-hydroxystyrene-methacrylic acid copolymers, p-hydroxy-styrene-methyl methacrylate copolymers, p-hydroxystyrene-acrylic acid-methyl methacrylate copolymers, p-hydroxy-styrene-methyl acrylate copolymers, p-hydroxystyrene-methacrylic acid-methyl methacrylate copolymers, poly(methacrylic acid), poly(acrylic acid), acrylic acid-methyl acrylate copolymers, methacrylic acid-methyl methacrylate copolymers, acrylic acid-maleimide copolymers, methacrylic acid-maleimide copolymers, p-hydroxystyrene-acrylic acid-maleimide copolymers, and p-hydroxystyrene-methacrylic acid-maleimide copolymers as well as dendritic and hyperbranched polymers thereof, but are not limited to these combinations.

Preferred are poly(p-hydroxystyrene), partially hydrogenated p-hydroxystyrene copolymers, p-hydroxystyrene-styrene copolymers, p-hydroxystyrene-acrylic acid copolymers, and p-hydroxystyrene-methacrylic acid copolymers as well as dendritic and hyperbranched polymers thereof.

Alkali-soluble resins comprising units of the following formula (2), (2') or (2") are especially preferred.

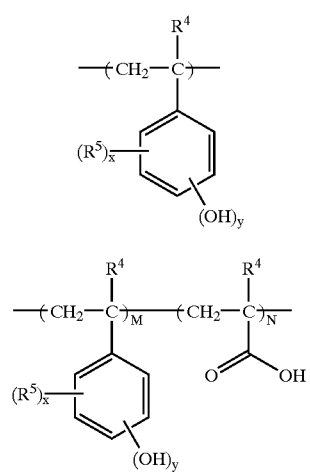

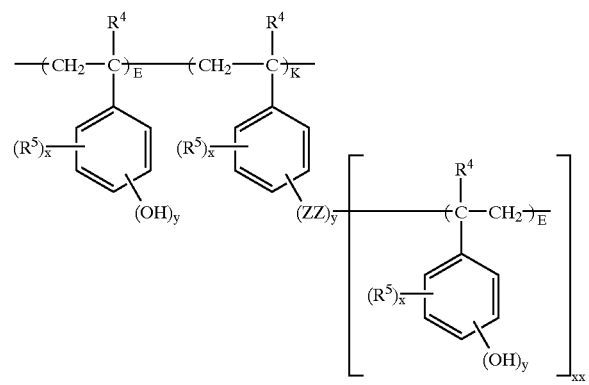

Herein $R^4$ is hydrogen or methyl, and $R^5$ is a straight, branched or cyclic alkyl group of 1 to 8 carbon atoms. Subscript x is 0 or a positive integer, and y is a positive integer, satisfying $x+y \leq 5$. Subscripts M and N are positive integers, satisfying $0 < N/(M+N) \leq 0.5$. ZZ is a divalent organic group selected from among $CH_2$, CH(OH), $CR^5$(OH), C=O and $C(OR^5)(OH)$ or a trivalent organic group represented by —C(OH)=. Subscript E, which may be identical or different, is a positive integer, and K is a positive integer, satisfying $0.001 \leq K/(K+E) \leq 0.1$, and XX is 1 or 2.

The alkali-soluble resins or polymers should preferably have a weight average molecular weight (Mw) of 3,000 to 100,000. Many polymers with Mw of less than 3,000 do not perform well and are poor in heat resistance and film formation. Many polymers with Mw of more than 100,000 give rise to a problem with respect to dissolution in the resist solvent and developer. The polymer should also preferably have a dispersity (Mw/Mn) of up to 3.5, and more preferably up to 1.5. With a dispersity of more than 3.5, resolution is low in many cases. Although the preparation method is not critical, a poly(p-hydroxystyrene) or similar polymer with a low dispersity or narrow dispersion can be synthesized by living anion polymerization.

The dendritic or hyperbranched polymer of phenol derivative represented by formula (2") can be synthesized by effecting living anion polymerization of a polymerizable monomer such as 4-tert-butoxystyrene and reacting a branching monomer such as chloromethylstyrene as appropriate during the living anion polymerization.

More particularly, living anion polymerization is started using a polymerizable monomer such as 4-tert-butoxystyrene. After a predetermined amount has been polymerized, a branching monomer such as chloromethylstyrene is introduced and reacted with the intermediate. Then the polymerizable monomer such as 4-tert-butoxystyrene and/or the branching monomer such as chloromethylstyrene is added again for polymerization. This operation is repeated many times until a desired dendritic or hyperbranched polymer is obtained. If necessary, the protective groups used to enable living polymerization are deblocked, yielding a dendritic or hyperbranched polymer of phenol derivative.

Examples of the branching monomer are given below.

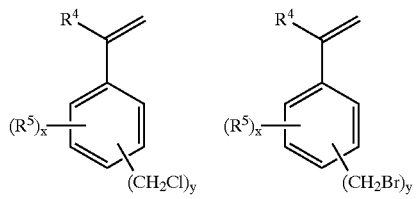

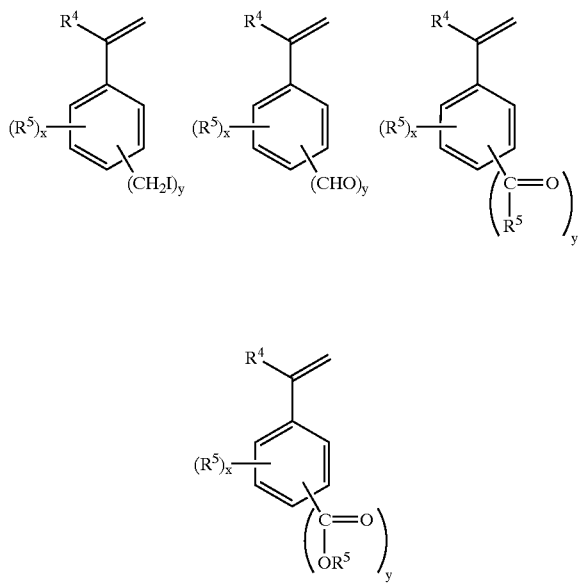

$R^4$, $R^5$, x and y are as defined above.

Illustrative examples of the dendritic or hyperbranched polymer are those having recurring units of the following approximate formulas (8) to (12).

(8)

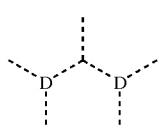
(9)

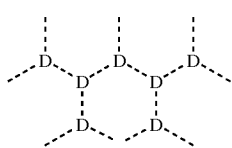
(10)

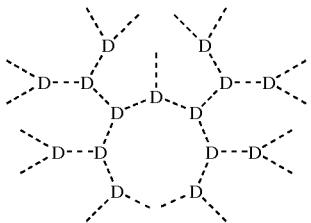
(11)

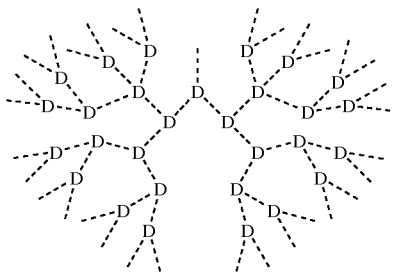
(12)

Herein, broken lines represent polymer chains of the phenol derivative monomer, and D represents units based on the branching monomer. The number of broken line segments between D and D is depicted merely for the sake of convenience, independent of the number of recurring units in the polymer chain included between D and D.

The dendritic or hyperbranched polymer of a phenol derivative is prepared by effecting living polymerization of the phenol derivative, reacting with a compound having a polymerizable moiety and a terminating moiety and proceeding further polymerization. By repeating this operation desired times, a dendritic or hyperbranched polymer of phenol derivative can be synthesized. The living polymerization may be effected by any desired technique although living anion polymerization is preferred because of ease of control.

For living anion polymerization to take place, the reaction solvent is preferably selected from toluene, benzene, tetrahydrofuran, dioxane, and diethyl ether. Of these, polar solvents such as tetrahydrofuran, dioxane, and diethyl ether are preferable. They may be used alone or in admixture of two or more.

The initiator used herein is preferably selected from sec-butyl lithium, n-butyl lithium, naphthalene sodium and cumyl potassium. The amount of the initiator used is proportional to the design molecular weight.

Preferred reaction conditions include a temperature of −80° C. to 100° C., preferably −70° C. to 0° C., and a time of about 0.1 to 50 hours, preferably about 0.5 to 5 hours.

One exemplary reaction scheme using sec-butyl lithium as the initiator and 4-chloromethylstyrene as the branching monomer is shown below. The branching coefficient can be altered by repeating the reaction step any desired times.

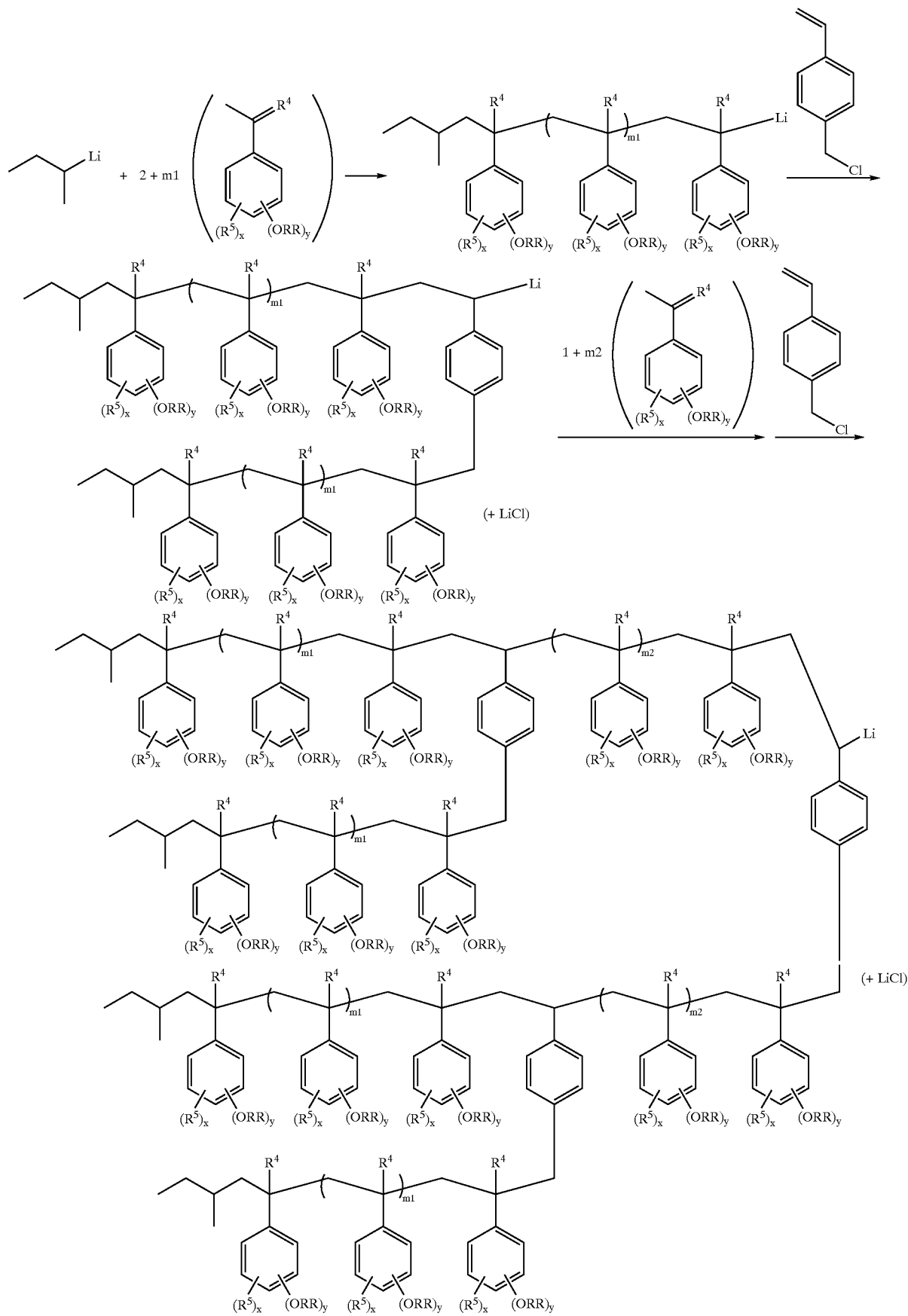

Herein, $R^4$, $R^5$, x and y are as defined above, $m_1$ and $m_2$ each are 0 or a positive integer, and RR is a substituent capable of withstanding living anion polymerization.

The living polymer thus obtained is deactivated or stopped, and the substituent RR which has been introduced for the progress of living anion polymerization is deblocked, obtaining an alkali-soluble resin.

The resin (A) is an alkali-soluble resin (as mentioned above) having hydroxyl or carboxyl groups, some of which are replaced by acid labile groups such that the solubility in an alkaline developer changes as a result of severing of the acid labile groups under the action of an acid generated by the photoacid generator upon exposure to radiation. Especially preferred is a polymer comprising recurring units of the above formula (2) or (2") and containing phenolic hydroxyl groups in which hydrogen atoms of the phenolic hydroxyl group are replaced by acid labile groups of one or more types in a proportion of more than 0 mol % to 80 mol % on the average of the entire hydrogen atoms of the phenolic hydroxyl group, the polymer having a weight average molecular weight of 3,000 to 100,000.

Also preferred is a polymer comprising recurring units of the above formula (2'), that is, a copolymer comprising p-hydroxystyrene and/or α-methyl-p-hydroxystyrene and acrylic acid and/or methacrylic acid, wherein some of the hydrogen atoms of carboxyl groups of the acrylic acid and/or methacrylic acid are replaced by acid labile groups of one or more types to form an ester, the units based on the acrylic ester and/or methacrylic ester are contained in a proportion of more than 0 mol % to 50 mol %, on the average, of the copolymer, and wherein some of the hydrogen atoms of the phenolic hydroxyl groups of p-hydroxystyrene and/or α-methyl-p-hydroxystyrene may be replaced by acid labile groups of one or more types. Further preferred is such a copolymer in which the units based on the acrylic ester and/or methacrylic ester and the p-hydroxystyrene and/or α-methyl-p-hydroxystyrene having acid labile groups substituted thereon are contained in a proportion of more than 0 mol % to 80 mol %, on the average, of the copolymer.

Exemplary such polymers are polymers comprising recurring units represented by the following general formula (2a), (2a') or (2a") and having a weight average molecular weight of 3,000 to 100,000.

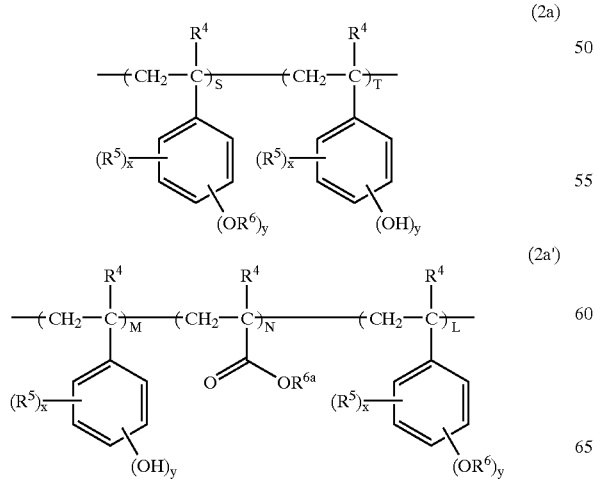

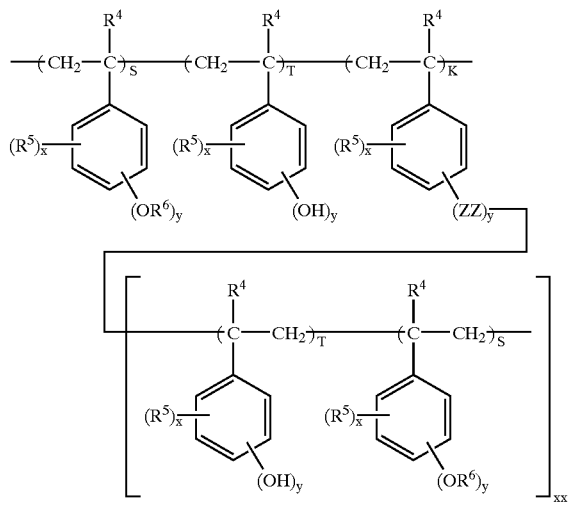

Herein, $R^4$ is hydrogen or methyl. $R^5$ is a straight, branched or cyclic alkyl group of 1 to 8 carbon atoms. $R^6$ is an acid labile group. $R^{6a}$ is hydrogen or an acid labile group, at least some, preferably all of the $R^{6a}$ groups are substituents of formula (1) and/or acid labile groups. Letter x is 0 or a positive integer, and y is a positive integer, satisfying $x+y \leq 5$. The $R^6$ groups may be the same or different when y is 2 or more. S and T are positive integers, satisfying $0.01 \leq S/(S+T) \leq 0.4$. M and N are positive integers, L is 0 or a positive integer, satisfying $0 < N/(M+N) \leq 0.4$ and $0.01 \leq (N+L)/(M+N+L) \leq 0.4$. ZZ is a divalent organic group selected from among $CH_2$, $CH(OH)$, $CR^5(OH)$, $C=O$ and $C(OR^5)(OH)$ or a trivalent organic group represented by $-C(OH)=$. Subscript E, which may be identical or different, is a positive integer, and K is a positive integer, satisfying $0.001 \leq K/(K+S+T) \leq 0.1$, and XX is 1 or 2.

$R^5$ stands for straight, branched or cyclic $C_{1-8}$ alkyl groups, for example, methyl, ethyl, propyl, isopropyl, n-butyl, isobutyl, tert-butyl, cyclohexyl and cyclopentyl.

The acid labile groups are selected from a variety of such groups. The preferred acid labile groups are groups of the following general formulae (4) to (7), tertiary alkyl group of 4 to 20 carbon atoms, preferably 4 to 15 carbon atoms, trialkylsilyl groups whose alkyl groups each have 1 to 6 carbon atoms, oxoalkyl groups of 4 to 20 carbon atoms, or aryl-substituted alkyl groups of 7 to 20 carbon atoms.

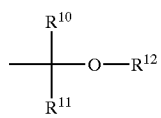

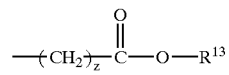

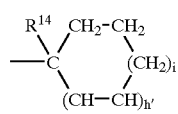

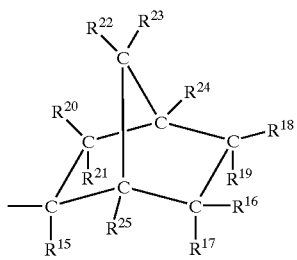

(7)

Herein $R^{10}$ and $R^{11}$ are independently hydrogen or straight, branched or cyclic alkyl groups of 1 to 18 carbon atoms, preferably 1 to 10 carbon atoms, for example, methyl, ethyl, propyl, isopropyl, n-butyl, sec-butyl, tert-butyl, cyclopentyl, cyclohexyl, 2-ethylhexyl and n-octyl. $R^{12}$ is a monovalent hydrocarbon group of 1 to 18 carbon atoms, preferably 1 to 10 carbon atoms, which may have a hetero atom (e.g., oxygen atom), for example, straight, branched or cyclic alkyl groups, and such groups in which some hydrogen atoms are replaced by hydroxyl, alkoxy, oxo, amino or alkylamino groups. Illustrative examples of the substituted alkyl groups are given below.

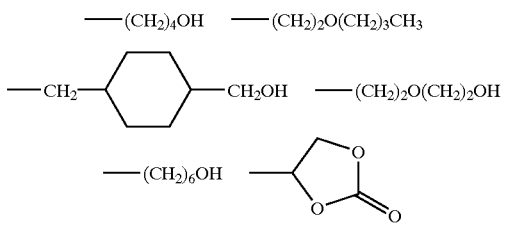

A pair of $R^{10}$ and $R^{11}$, a pair of $R^{10}$ and $R^{12}$, or a pair of $R^{11}$ and $R^{12}$, taken together, may form a ring. Each of $R^{10}$, $R^{11}$ and $R^{12}$ is a straight or branched alkylene group of 1 to 18 carbon atoms, preferably 1 to 10 carbon atoms, when they form a ring.

$R^{13}$ is a tertiary alkyl group of 4 to 20 carbon atoms, preferably 4 to 15 carbon atoms, a trialkylsilyl group whose alkyl groups each have 1 to 6 carbon atoms, an oxoalkyl group of 4 to 20 carbon atoms or a group of formula (4). Exemplary tertiary alkyl groups are tert-butyl, tert-amyl, 1,1-diethylpropyl, 1-methylcyclopentyl, 1-ethylcyclopentyl, 1-isopropylcyclopentyl, 1-butylcyclopentyl, 1-methylcyclohexyl, 1-ethylcyclohexyl, 1-isopropylcyclohexyl, 1-butylcyclohexyl, 1-ethyl-2-cyclopentenyl, 1-ethyl-2-cyclohexenyl, and 2-methyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxoxan-4-yl, and 5-methyl-5-oxooxolan-4-yl. Letter z is an integer of 0 to 6.

$R^{14}$ is a straight, branched or cyclic alkyl group of 1 to 8 carbon atoms or substituted or unsubstituted aryl group of 6 to 20 carbon atoms. Exemplary straight, branched or cyclic alkyl groups include methyl, ethyl, propyl, isopropyl, n-butyl, sec-butyl, tert-butyl, tert-amyl, n-pentyl, n-hexyl, cyclopentyl, cyclohexyl, cyclopentylmethyl, cyclopentylethyl, cyclohexylmethyl and cyclohexylethyl. Exemplary substituted or unsubstituted aryl groups include phenyl, methylphenyl, naphthyl, anthryl, phenanthryl, and pyrenyl. Letter h' is equal to 0 or 1, i is equal to 0, 1, 2 or 3, satisfying 2h'+i=2 or 3.

$R^{15}$ is a straight, branched or cyclic alkyl group of 1 to 8 carbon atoms or substituted or unsubstituted aryl group of 6 to 20 carbon atoms, examples of which are as exemplified for $R^{14}$, $R^{16}$ to $R^{25}$ are independently hydrogen or monovalent hydrocarbon groups of 1 to 15 carbon atoms which may contain a hetero atom, for example, straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl, and cyclohexylbutyl, and substituted ones of these groups in which some hydrogen atoms are replaced by hydroxyl, alkoxy, carboxy, alkoxycarbonyl, oxo, amino, alkylamino, cyano, mercapto, alkylthio, and sulfo groups. $R^{16}$ to $R^{25}$, for example, a pair of $R^{16}$ and $R^{17}$, a pair of $R^{16}$ and $R^{18}$, a pair of $R^{17}$ and $R^{19}$, a pair of $R^{18}$ and $R^{19}$, a pair of $R^{20}$ and $R^{21}$, or a pair of $R^{22}$ and $R^{23}$, taken together, may form a ring. When $R^{16}$ to $R^{25}$ form a ring, they are divalent $C_{1-15}$ hydrocarbon groups which may contain a hetero atom, examples of which are the above-exemplified monovalent hydrocarbon groups with one hydrogen atom eliminated. Also, two of $R^{16}$ to $R^{25}$ which are attached to adjacent carbon atoms (for example, a pair of $R^{16}$ and $R^{18}$, a pair of $R^{18}$ and $R^{24}$, or a pair of $R^{22}$ and $R^{24}$) may directly bond together to form a double bond.

Of the acid labile groups of formula (4), illustrative examples of the straight or branched groups are given below.

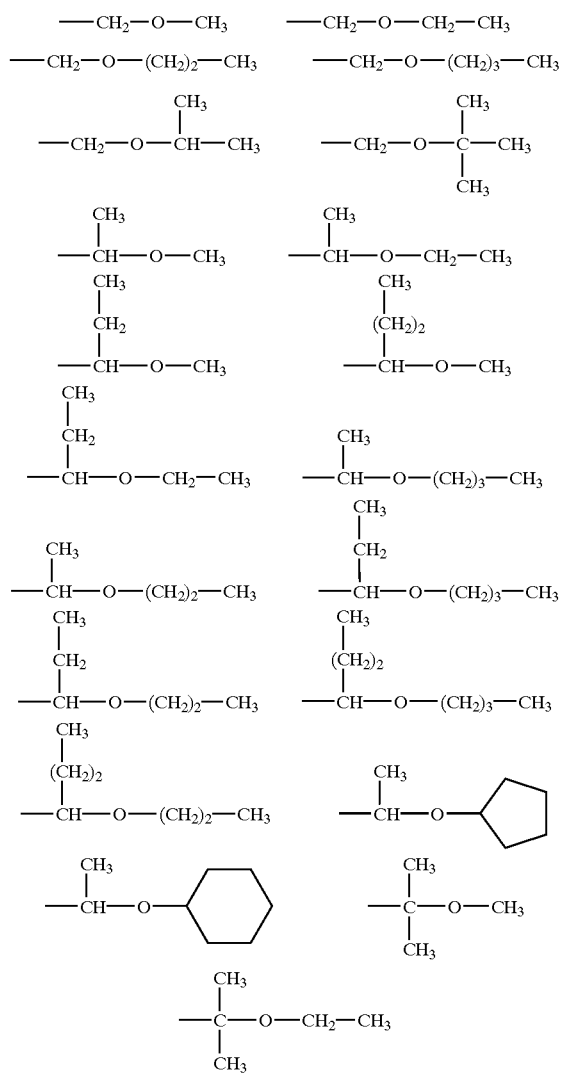

Of the acid labile groups of formula (4), illustrative examples of the cyclic groups include tetrahydrofuran-2-yl, 2-methyltetrahydrofuran-2-yl, tetrahydropyran-2-yl and 2-methyltetrahydropyran-2-yl.

Illustrative examples of the acid labile groups of formula (5) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyl-oxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl.

Illustrative examples of the acid labile groups of formula (6) include 1-methylcyclopentyl, 1-ethylcyclopentyl, 1-n-propylcyclopentyl, 1-isopropylcyclopentyl, 1-n-butyl-cyclopentyl, 1-sec-butylcyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl.

Illustrative examples of the acid labile groups of formula (7) are given below.

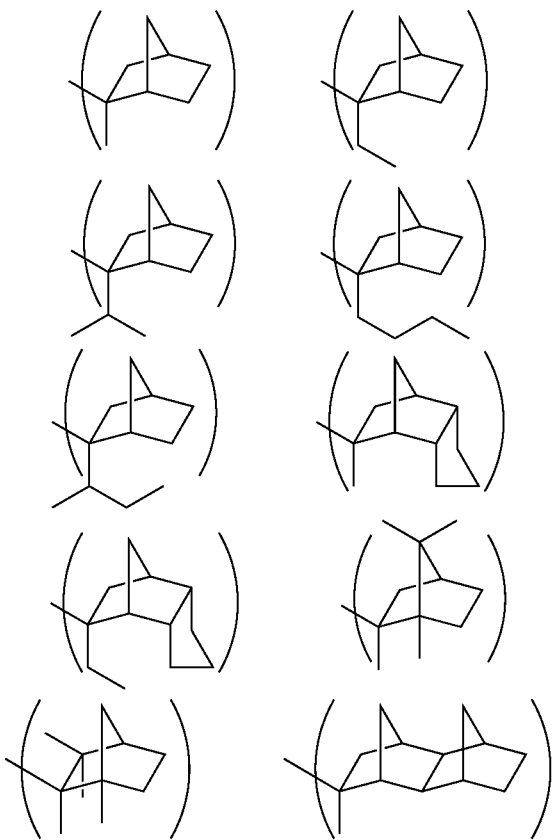

Exemplary of the tertiary alkyl group of 4 to 20 carbon atoms, preferably 4 to 15 carbon atoms, are tert-butyl, tert-amyl, 3-ethyl-3-pentyl and dimethylbenzyl.

Exemplary of the trialkylsilyl groups whose alkyl groups each have 1 to 6 carbon atoms are trimethylsilyl, triethylsilyl, and tert-butyldimethylsilyl.

Exemplary of the oxoalkyl groups of 4 to 20 carbon atoms are 3-oxocyclohexyl and groups represented by the following formulae.

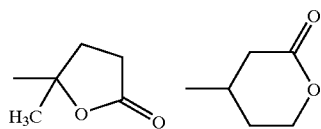

Exemplary of the aryl-substituted alkyl groups of 7 to 20 carbon atoms are benzyl, methylbenzyl, dimethylbenzyl, diphenylmethyl, and 1,1-diphenylethyl.

In the resist composition comprising an onium salt of formula (1), (1a), (1a') or (1b), the resin (A) may be the polymer of formula (2) or (2') in which some of the hydrogen atoms of the phenolic hydroxyl groups and/or all of the carboxyl groups are partially replaced by acid labile groups of one or more types, and the hydrogen atoms of the remaining phenolic hydroxyl groups are crosslinked within a molecule and/or between molecules, in a proportion of more than 0 mol % to 50 mol %, on the average, of the entire phenolic hydroxyl groups on the polymer, with crosslinking groups having C—O—C linkages represented by the following general formula (3a) or (3b).

The crosslinking groups having C—O—C linkages include groups represented by the following general formula (3a) or (3b).

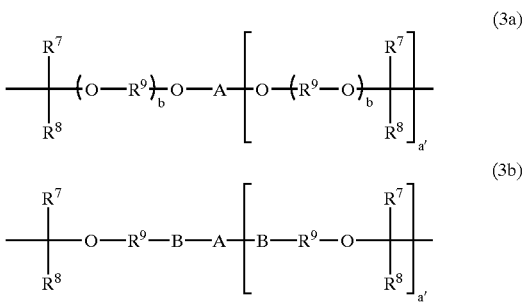

Herein, each of $R^7$ and $R^8$ is hydrogen or a straight, branched or cyclic alkyl group of 1 to 8 carbon atoms, or $R^7$ and $R^8$, taken together, may form a ring, and each of $R^7$ and $R^8$ is a straight or branched alkylene group of 1 to 8 carbon atoms when they form a ring. $R^9$ is a straight, branched or cyclic alkylene group of 1 to 10 carbon atoms, letter b is 0 or an integer of 1 to 10. Letter a' is an integer of 1 to 7 and preferably 1 to 3, and b is 0 or an integer of 1 to 10 and preferably 0 or an integer of 1 to 5. A is an (a'+1)-valent aliphatic or alicyclic saturated hydrocarbon group, aromatic hydrocarbon group or heterocyclic group of 1 to 50 carbon atoms, which may be separated by a hetero atom and in which some of the hydrogen atoms attached to carbon atoms may be replaced by hydroxyl, carboxyl, carbonyl or halogen. B is —CO—O—, —NHCO—O— or —NHCONH—.

Examples of the straight, branched or cyclic $C_{1-8}$ alkyl group represented by $R^7$ and $R^8$ are as exemplified for $R^5$.

Examples of the straight, branched or cyclic $C_{1-10}$ alkylene group represented by $R^9$ include methylene, ethylene, propylene, isopropylene, n-butylene, isobutylene, cyclohexylene, and cyclopentylene.

Exemplary halogen atoms are fluorine, chlorine, bromine and iodine.

Illustrative examples of A are described later. These crosslinking groups of formulae (3a) and (3b) originate from alkenyl ether compounds and halogenated alkyl ether compounds to be described later.

As understood from the value of a' in formula (3a) or (3b), the crosslinking group having C—O—C linkages is not limited to a divalent one and trivalent to octavalent groups are acceptable. The detail of the crosslinking group is described in JP-A 2000-194127, which is incorporated herein by reference. Some preferred examples are given below.

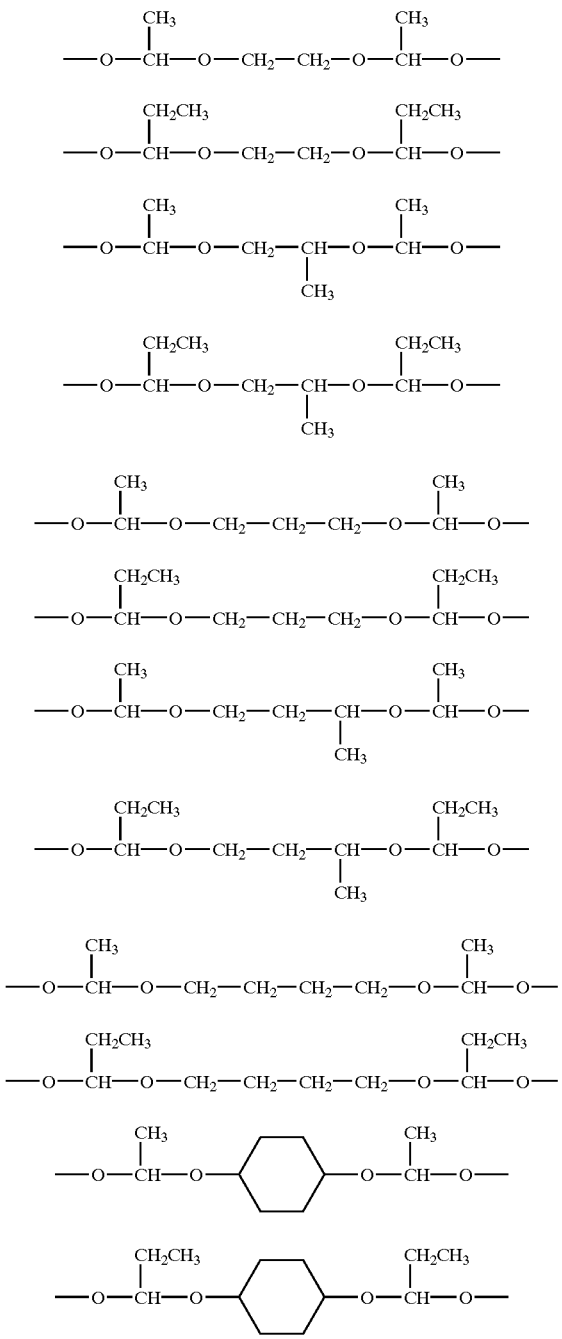

In the resist composition of the invention, the preferred polymer is a polymer comprising recurring units of the following general formula (2b), (2b') or (2b"), and more preferably the same polymer in which hydrogen atoms of phenolic hydroxyl groups represented by R are eliminated to leave oxygen atoms which are crosslinked within a molecule and/or between molecules with crosslinking groups having C—O—C linkages represented by the above formula (3a) or (3b).

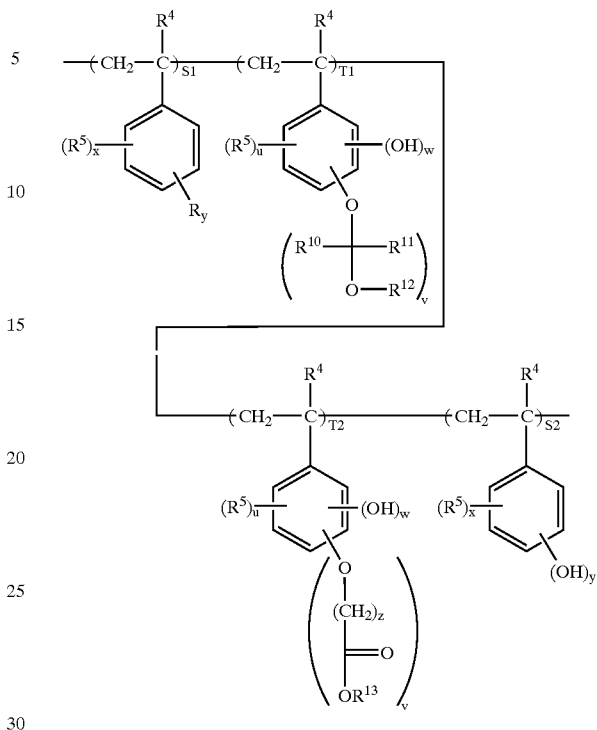

(2b)

Herein, R represents a hydroxyl group or an acid labile group having an oxygen atom attached thereto (i.e., —O-acid labile group) other than —OCR$^{10}$R$^{11}$OR$^{12}$ and —O(CH$_2$)$_z$COOR$^{13}$. R$^4$ is hydrogen or methyl, R$^5$ is a straight, branched or cyclic alkyl group of 1 to 8 carbon atoms. R$^{10}$ and R$^{11}$ are independently hydrogen or straight, branched or cyclic alkyl groups of 1 to 18 carbon atoms, R$^{12}$ is a monovalent hydrocarbon group of 1 to 18 carbon atoms which may have a hetero atom, or a pair of R$^{10}$ and R$^{11}$, R$^{10}$ and R$^{12}$, or R$^{11}$ and R$^{12}$, taken together, may form a ring, with the proviso that each of R$^{10}$, R$^{11}$ and R$^{12}$ is a straight or branched alkylene group of 1 to 18 carbon atoms when they form a ring. R$^{13}$ is a tertiary alkyl group of 4 to 20 carbon atoms, an aryl-substituted alkyl group of 7 to 20 carbon atoms, an oxoalkyl group of 4 to 20 carbon atoms or a group represented by —CR$^{10}$R$^{11}$OR$^{12}$. Letter z is an integer of 0 to 6. S2 is a positive number, each of S1, T1, and T2 is 0 or a positive number, satisfying 0≦S1/(S1+T1+T2+S2)≦0.8, 0≦T1/(S1+T1+T2+S2)≦0.8, 0≦T2/(S1+T1+T2+S2)≦0.8, and S1+T1+T2+S2=1. T1 and T2 are not equal to 0 at the same time. Each of u and w is 0 or a positive integer, and v is a positive integer, satisfying u+v+w≦5. Letters x and y are as defined above.

More preferably, S1, S2, T1 and T2 satisfy the following ranges.

0≦S1/(S1+T1+T2+S2)≦0.5,
   especially 0.002≦S1/(S1+T1+T2+S2)≦0.2
0≦T1/(S1+T1+T2+S2)≦0.5,
   especially 0≦T1/(S1+T1+T2+S2)≦0.4
0≦T2/(S1+T1+T2+S2)≦0.5,
   especially 0≦T2/(S1+T1+T2+S2)≦0.4
0.4≦S2/(S1+T1+T2+S2)<1,
   especially 0.5≦S2/(S1+T1+T2+S2)≦0.9
0<(T1+T2)/(S1+T1+T2+S2)≦0.5,
   especially 0.1≦(T1+T2)/(S1+T1+T2+S2)≦0.4

It is also preferred that T1/(T1+T2) be from 0 to 1, more preferably from 0.5 to 1, and most preferably from 0.7 to 1.

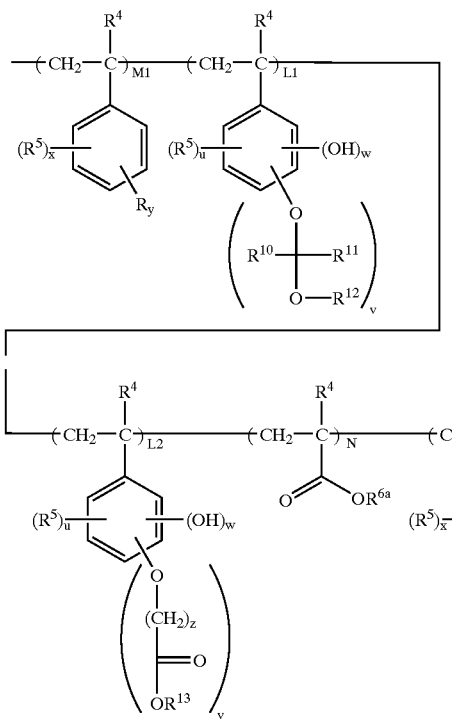

(2b′)

Herein, R, $R^4$, $R^5$, $R^{10}$, $R^{11}$, $R^{12}$, $R^{13}$ z, u, v, and w are as defined above. $R^{6a}$ is hydrogen or an acid labile group as mentioned above, and at least some, preferably all of the $R^{6a}$ groups are acid labile groups. M2 is a positive number, each of M1, L1, L2 and N is 0 or a positive number, satisfying $0 \leq M1/(M1+L1+L2+N+M2) \leq 0.8$, $0 \leq L1/(M1+L1+L2+N+M2) \leq 0.8$, $0 \leq L2/(M1+L1+L2+N+M2) \leq 0.8$, $0 \leq N/(M1+L1+L2+N+M2) \leq 0.8$, and $M1+L1+L2+N+M2=1$, L1, L2 and N are not equal to 0 at the same time.

More preferably, M1, L1, L2, N and M2 satisfy the following ranges.

$0 \leq M1/(M1+L1+L2+N+M2) \leq 0.5$,
especially $0.002 \leq M1/(M1+L1+L2+N+M2) \leq 0.2$ $0 \leq L1/(M1+L1+L2+N+M2) \leq 0.5$,
especially $0 \leq L1(M1+L1+L2+N+M2) \leq 0.4$ $0 \leq L2/(M1+L1+L2+N+M2) \leq 0.5$,
especially $0 \leq L2/(M1+L1+L2+N+M2) \leq 0.4$ $0 \leq N/(M1+L1+L2+N+M2) \leq 0.5$,
especially $0 \leq N/(M1+L1+L2+N+M2) \leq 0.4$ $0.4 \leq M2/(M1+L1+L2+N+M2) < 1$,
especially $0.5 \leq M2/(M1+L1+L2+N+M2) \leq 0.9$ $0 < (L1+L2+N)/(M1+L1+L2+N+M2) \leq 0.5$,
especially $0.1 \leq (L1+L2+N)/(M1+L1+L2+N+M2) \leq 0.4$ It is also preferred that N/(L1+L2+N) be from 0 to 1, more preferably from 0.5 to 1, and most preferably from 0.7 to 1.

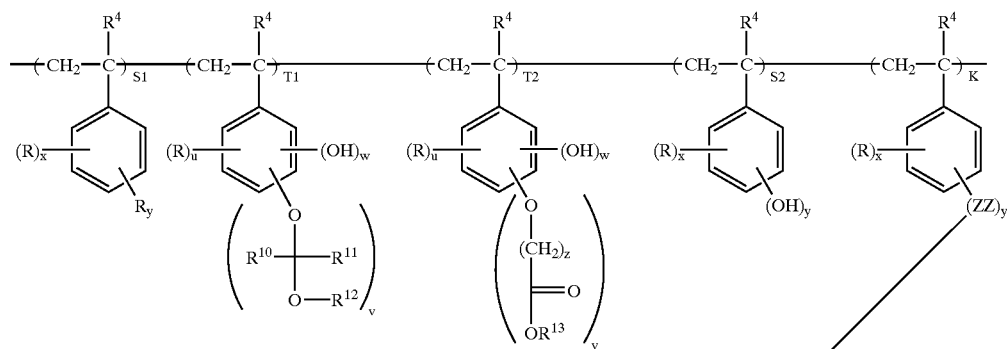

(2b″)

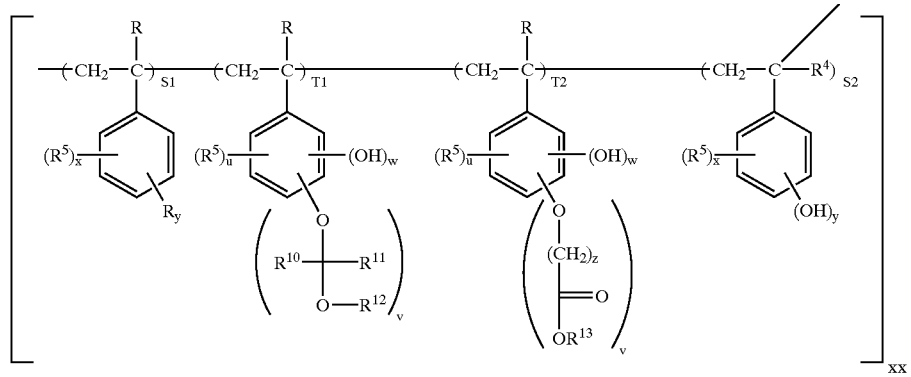

Herein, R, $R^4$, $R^5$, $R^{10}$, $R^1$, $R^{12}$, $R^{13}$, S1, S2, T1, T2, u, w, v, n, x, y, and z are as defined above. ZZ is a divalent organic group selected from among $CH_2$, CH(OH), $CR^5$(OH), C=O and $C(OR^5)$(OH) or a trivalent organic group represented by —C(OH)=. Subscript XX is 1 or 2, and K is a positive integer, satisfying $0.001 \leq K/(S1+T1+T2+S2+K) \leq 0.1$.

In this polymer as well, the total amount of the acid labile groups and crosslinking groups is, on the average, more than 0 mol % to 80 mol % and especially 2 to 50 mol %, based on the entire phenolic hydroxyl groups in formula (2b) or (2b") or the phenolic hydroxyl groups and carboxyl groups in formula (2b') combined.

An appropriate proportion of crosslinking groups having C—O—C linkages is, on the average, from more than 0 mol % to 50 mol %, and especially from 0.2 to 20 mol %. With 0 mol %, few benefits of the crosslinking group are obtained, resulting in a reduced contrast of alkali dissolution rate and a low resolution. With more than 50 mol %, a too much crosslinked polymer would gel, become insoluble in alkali, induce a film thickness change, internal stresses or bubbles upon alkali development, and lose adhesion to the substrate due to less hydrophilic groups.

The proportion of acid labile groups is on the average preferably from more than 0 mol % to 80 mol %, especially from 10 to 50 mol %. With 0 mol %, there may result a reduced contrast of alkali dissolution rate and low resolution. With more than 80 mol %, there may result a loss of alkali dissolution, less affinity to an alkali developer upon development, and a low resolution.

By properly selecting the proportions of crosslinking groups having C—O—C linkages and acid labile groups within the above-defined ranges, it becomes possible to control the size and configuration of a resist pattern as desired. In the resist composition comprising the onium salt according to the invention, the contents of crosslinking groups having C—O—C linkages and acid labile groups in the polymer have substantial influence on the dissolution rate contrast of a resist film and govern the properties of the resist composition relating to the size and configuration of a resist pattern.

Now "A" in the crosslinking group is described. The (a'+1)-valent organic groups represented by A include hydrocarbon groups, for example, substituted or unsubstituted alkylene groups preferably having 1 to 50 carbon atoms, and especially 1 to 40 carbon atoms, substituted or unsubstituted arylene groups preferably having 6 to 50 carbon atoms, and especially 6 to 40 carbon atoms (these alkylene and arylene groups may have an intervening hetero atom or group such as O, NH, $N(CH_3)$, S or $SO_2$, and where substituted, the substituents are hydroxyl, carboxyl, acyl and fluorine), and combinations of these alkylene groups with these arylene groups. Additional examples include (a'+1)-valent heterocyclic groups, and combinations of these heterocyclic groups with the foregoing hydrocarbon groups.

Illustrative examples of A are described in JP-A 2000-194127. Preferred are those of formula (3a) wherein $R^{11}$ is methyl, $R^{12}$ is hydrogen, a' is 1, b is 0, and A is ethylene, 1,4-butylene or 1,4-cyclohexylene.

In preparing the polymer which is crosslinked within a molecular and/or between molecules with crosslinking groups having C—O—C linkages, synthesis may be made by reacting a corresponding non-crosslinked polymer with an alkenyl ether in the presence of an acid catalyst in a conventional manner.

Alternatively, where decomposition of other acid labile groups takes place in the presence of an acid catalyst, the end product can be synthesized by first reacting an alkenyl ether with hydrochloric acid or the like to form a halogenated alkyl ether, and reacting it with a polymer under basic conditions in a conventional manner.

Illustrative examples of the alkenyl ether are described in JP-A 2000-194127. Preferred among these are ethylene glycol divinyl ether, 1,2-propanediol divinyl ether, 1,3-propanediol divinyl ether, 1,3-butanediol divinyl ether, 1,4-butanediol divinyl ether, and 1,4-cyclohexanediol divinyl ether.

In the resist composition comprising the onium salt according to the invention, the resin used as component (A) is as described above while the preferred acid labile groups introduced therein are 1-ethylcyclohexyl, 1-ethylcyclopentyl, 1-ethylcyclohexylcarbonylmethyl, tert-amyl, 1-ethoxyethyl, 1-ethoxypropyl, tetrahydrofuranyl, tetrahydropyranyl, tert-butyl, tert-butoxycarbonyl, tert-butoxycarbonylmethyl groups, and substituents of formula (3a) wherein $R^7$ is methyl, $R^8$ is hydrogen, a' is 1, b is 0, and A is ethylene, 1,4-butylene or 1,4-cyclohexylene.

In a single polymer, these substituents may be incorporated alone or in admixture of two or more types. A blend of two or more polymers having substituents of different types is also acceptable.

Appropriate combinations of substituents of two or more types include a combination of acetal with acetal analog, a combination of acetal with a substituent having a different degree of scission by acid such as tert-butoxy, a combination of a crosslinking acid labile group with acetal, and a combination of a crosslinking acid labile group with a substituent having a different degree of scission by acid such as tert-butoxy.

The percent proportion of these substituents substituting for phenol and carboxyl groups in the polymer is not critical. Preferably the percent substitution is selected such that when a resist composition comprising the polymer is applied onto a substrate to form a coating, the unexposed area of the coating may have a dissolution rate of 0.01 to 10 Å/sec in a 2.38% tetramethylammonium hydroxide (TMAH) developer.

On use of a polymer containing a greater proportion of carboxyl groups which can reduce the alkali dissolution rate, the percent substitution must be increased or non-acid-labile substituents to be described later must be introduced.

When acid labile groups for intramolecular and/or intermolecular crosslinking are to be introduced, the percent proportion of crosslinking substituents is preferably up to 20%, more preferably up to 10%. If the percent substitution of crosslinking substituents is too high, crosslinking results in a higher molecular weight which can adversely affect dissolution, stability and resolution. It is also preferred to further introduce another non-crosslinking acid labile group into the crosslinked polymer at a percent substitution of up to 10% for adjusting the dissolution rate to fall within the above range.

In the case of poly(p-hydroxystyrene), the optimum percent substitution differs between a substituent having a strong dissolution inhibitory action such as a tert-butoxycarbonyl group and a substituent having a weak dissolution inhibitory action such as an acetal group although the overall percent substitution is preferably 10 to 40%, more preferably 20 to 30%.

Polymers having such acid labile groups introduced therein should preferably have a weight average molecular weight (Mw) of 3,000 to 100,000. With a Mw of less than 3,000, polymers would perform poorly and often lack heat resistance and film formability. Polymers with a Mw of more than 100,000 would be less soluble in a developer and a resist solvent.

Where non-crosslinking acid labile groups are introduced, the polymer should preferably have a dispersity (Mw/Mn) of up to 3.5, preferably up to 1.5. A polymer with a dispersity of more than 3.5 often results in a low resolution. Where crosslinking acid labile groups are introduced, the starting alkali-soluble resin should preferably have a dispersity (Mw/Mn) of up to 1.5, and the dispersity is kept at 3 or lower even after protection with crosslinking acid labile groups. If the dispersity is higher than 3, dissolution, coating, storage stability and/or resolution is often poor.

To impart a certain function, suitable substituent groups may be introduced into some of the phenolic hydroxyl and carboxyl groups on the acid labile group-protected polymer. Exemplary are substituent groups for improving adhesion to the substrate, non-acid-labile groups for adjusting dissolution in an alkali developer, and substituent groups for improving etching resistance. Illustrative, non-limiting, substituent groups include 2-hydroxyethyl, 2-hydroxypropyl, methoxymethyl, methoxycarbonyl, ethoxycarbonyl, methoxycarbonylmethyl, ethoxycarbonylmethyl, 4-methyl-2-oxo-4-oxolanyl, 4-methyl-2-oxo-4-oxanyl, methyl, ethyl, propyl, n-butyl, sec-butyl, acetyl, pivaloyl, adamantyl, isobornyl, and cyclohexyl.

Illustrative examples of the onium salts of formulae (1), (1a), (1a') and (1b) as the photoacid generator (B) are as described above, and combinations of cations with anions are listed below again.

Examples of the sulfonate anion include 3-methoxy-4-(4'-methylphenylsulfonyloxy)benzenesulfonate, 3-methoxy-4-phenylsulfonyloxybenzenesulfonate, 3-methoxy-4-(2',4',6'-trimethylphenylsulfonyloxy) benzenesulfonate, 3-methoxy-4-(2'-naphthylsulfonyloxy) benzenesulfonate, 3-methoxy-4-(1'-naphthylsulfonyloxy) benzenesulfonate, 2-hydroxy-5-(4'-methylphenylsulfonyloxy)benzenesulfonate, 5-hydroxy-2-(4'-methylphenylsulfonyloxy)benzenesulfonate, 3-nitro-4-(4'-methylphenylsulfonyloxy)benzenesulfonate, 3-nitro-4-phenylsulfonyloxybenzenesulfonate, 3-nitro-4-(2',4',6'-trimethylphenylsulfonyloxy)benzenesulfonate, 3-nitro-4-(2'-naphthylsulfonyloxy)benzenesulfonate, 3-nitro-4-(1'-naphthylsulfonyloxy)benzenesulfonate, 3,5-dichloro-2-(4'-methylphenylsulfonyloxy)benzenesulfonate, 3,5-dichloro-2-phenylsulfonyloxybenzenesulfonate, 3,5-dichloro-2-(2',4',6'-trimethylphenylsulfonyloxy)benzenesulfonate, 3,5-dichloro-2-(2'-naphthylsulfonyloxy )benzenesulfonate, and 3,5-dichloro-2-(1'-naphthylsulfonyloxy)benzenesulfonate. Of these, 3-methoxy-4-(4'-methylphenylsulfonyloxy) benzenesulfonate, 3-methoxy-4-phenylsulfonyloxy) benzenesulfonate, 3-nitro-4-(4'-methylphenylsulfonyloxy) benzenesulfonate, and 3,5-dichloro-2-(4'-methylphenylsulfonyloxy)benzenesulfonate are preferred.

Exemplary iodonium cations include diphenyliodonium, bis(4-tert-butylphenyl)iodonium, 4-methoxyphenylphenyliodonium, 4-ethoxyphenylphenyliodonium, and 4-tert-butoxyphenylphenyliodonium, with the diphenyliodonium and bis(4-tert-butoxyphenyl)iodonium are preferred.

Exemplary sulfonium cations include triphenylsulfonium, 4-hydroxyphenyldiphenylsulfonium, (4-methylphenyl) diphenylsulfonium, bis(4-methylphenyl)phenyl-sulfonium, tris(4-methylphenyl)sulfonium, (4-methoxyphenyl) diphenylsulfonium, bis(4-methoxyphenyl)-phenylsulfonium, tris(4-methoxyphenyl)sulfonium, (4-tert-butylphenyl)diphenylsulfonium, bis(4-tert-butylphenyl)-phenylsulfonium, tris(4-tert-butylphenyl)sulfonium, (4-tert-butoxyphenyl)diphenylsulfonium, bis(4-tert-butoxyphenyl)-phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl) sulfonium, (3,4-di-tert-butoxyphenyl)diphenylsulfonium, bis(3,4-di-tert-butoxyphenyl)phenylsulfonium, tris(3,4-di-tert-butoxy-phenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 2-naphthyldiphenyl-sulfonium, dimethyl-2-naphthylsulfonium, 4-hydroxyphenyldimethylsulfonium, 4-methoxyphenyldimethylsulfonium, dimethylphenylsulfonium, diphenylmethylsulfonium, trimethylsulfonium, 2-oxocyclohexylcyclohexylmethylsulfonium, 2-oxocyclohexyl-methyl-phenylsulfonium, 2-oxocyclopentyl-methyl-phenylsulfonium, 2-oxocyclopropyl-methyl-phenylsulfonium, and tribenzyl-sulfonium. Of these, triphenylsulfonium, 4-tert-butoxyphenyldiphenylsulfonium, dimethylphenylsulfonium, and 4-tert-butylphenyldiphenyl-sulfonium are preferred.

Especially useful onium salts are:

triphenylsulfonium 3-methoxy-4-(4'-methylphenylsulfonyloxy)-benzenesulfonate,
4-tert-butoxyphenyldiphenylsulfonium 3-methoxy-4-(4'-methyl-phenylsulfonyloxy)benzenesulfonate,
4-tert-butylphenyldiphenylsulfonium 3-methoxy-4-(4'-methylphenylsulfonyloxy)benzenesulfonate,
dimethylphenylsulfonium 3-methoxy-4-(4'-methylphenylsulfonyloxy)benzenesulfonate,
tris(4-tert-butoxyphenyl)sulfonium 3-methoxy-4-(4'-methylphenylsulfonyloxy)benzenesulfonate,
tris(4-tert-butylphenyl)sulfonium 3-methoxy-4-(4'-methylphenylsulfonyloxy)benzenesulfonate,
tris(4-methylphenyl)sulfonium 3-methoxy-4-(4'-methylphenyl-sulfonyloxy)benzenesulfonate,
bis(4-tert-butylphenyl)iodonium 3-methoxy-4-(4'-methyl-phenylsulfonyloxy)benzenesulfonate,
diphenyliodonium 3-methoxy-4-(4'-methylphenylsulfonyloxy)-benzenesulfonate,
triphenylsulfonium 3-nitro-4-(4'-methylphenylsulfonyloxy)-benzenesulfonate,
4-tert-butoxyphenyldiphenylsulfonium 3-nitro-4-(4'-methyl-phenylsulfonyloxy)benzenesulfonate,
4-tert-butylphenyldiphenylsulfonium 3-nitro-4-(4'-methyl-phenylsulfonyloxy)benzenesulfonate,
dimethylphenylsulfonium 3-nitro-4-(4'-methylphenylsulfonyl-oxy)benzenesulfonate,
tris(4-tert-butoxyphenyl)sulfonium 3-nitro-4-(4'-methyl-phenylsulfonyloxy)benzenesulfonate,
tris(4-tert-butylphenyl)sulfonium 3-nitro-4-(4'-methyl-phenylsulfonyloxy)benzenesulfonate,
tris(4-methylphenyl)sulfonium 3-nitro-4-(4'-methylphenyl-sulfonyloxy)benzenesulfonate,
bis(4-tert-butylphenyl)iodonium 3-nitro-4-(4'-methylphenyl-sulfonyloxy)benzenesulfonate, and
diphenyliodonium 3-nitro-4-(4'-methylphenylsulfonyloxy)-benzenesulfonate.

In the chemical amplification type resist composition, an appropriate amount of the onium salt (B) of formula (1), (1a), (1a') or (1b) added is from 0.5 part to 20 parts by weight, and preferably from 1 to 10 parts by weight, per 100 parts by weight of the solids in the composition. The photoacid generators may be used alone or in admixture of two or more. The transmittance of the resist film can be controlled by using a photoacid generator having a low transmittance at the exposure wavelength and adjusting the amount of the photoacid generator added.

Component (C)

In one preferred embodiment, the resist composition further contains (C) a compound capable of generating an acid upon exposure to high energy radiation, that is, a second photoacid generator other than the onium salt (B). The second photoacid generators include sulfonium salts and iodonium salts as well as sulfonyldiazomethane, N-sulfonyloxyimide, benzoinsulfonate, nitrobenzylsulfonate, sulfone, and glyoxime derivatives. They may be used alone or in admixture of two or more. Exemplary photoacid generators are described in JP-A 2000-194127, though not limited thereto.

Preferred photoacid generators used herein are sulfonium salts and bissulfonyldiazomethanes.

Sulfonium salts are salts of sulfonium cations with sulfonate anions. In addition to those exemplified in connection with formulae (1), (1a) and (1a'), exemplary sulfonium cations include triphenylsulfonium, 4-tert-butoxyphenyldiphenylsulfonium, dimethylphenylsulfonium, 4-tert-butylphenyldiphenylsulfonium, tris(4-tert-butylphenyl)sulfonium and tris(4-methylphenyl)sulfonium. Exemplary sulfonate anions include benzenesulfonate, toluenesulfonate, trifluoromethylbenzenesulfonate, pentafluorobenzenesulfonate, 2,2,2-trifluoroethanesulfonate, nonafluorobutanesulfonate, heptadecafluorooctanesulfonate, and camphorsulfonate anions.

Exemplary bissulfonyldiazomethane compounds include bis(tert-butylsulfonyl)diazomethane, bis(cyclohexylsulfonyl)diazomethane, bis(tert-amylsulfonyl) diazomethane, bis(phenylsulfonyl)diazomethane, bis(4-methylphenylsulfonyl)diazomethane, bis(4-tert-butylphenylsulfonyl)diazomethane, and bis(2,4-dimethylphenylsulfonyl)diazomethane.

While the anion of the optimum acid to be generated differs depending on the ease of scission of acid labile groups introduced in the polymer, an anion which is nonvolatile and not extremely diffusive is generally chosen. The preferred anions include benzenesulfonic acid anions, toluenesulfonic acid anions, pentafluorobenzenesulfonic acid anions, 2,2,2-trifluoroethanesulfonic acid anions, nonafluorobutanesulfonic acid anions, heptadecafluorooctanesulfonic acid anions, and camphorsulfonic acid anions. Sulfonium and iodonium salts having these anions are especially preferred.

In the resist composition comprising the onium salt of formula (1), (1a), (1a') or (1b) as the first photoacid generator according to the invention, an appropriate amount of the second photoacid generator (C) is 0 to 20 parts, and especially 1 to 10 parts by weight per 100 parts by weight of the solids in the composition. The second photoacid generators may be used alone or in admixture of two or more. The transmittance of the resist film can be controlled by using a (second) photoacid generator having a low transmittance at the exposure wavelength and adjusting the amount of the photoacid generator added.

In the resist composition according to the invention, there may be added a compound which is decomposed with an acid to generate an acid, that is, acid-propagating compound. For these compounds, reference should be made to J. Photopolym. Sci. and Tech., 8, 43–44, 45–46 (1995), and ibid., 9, 29–30 (1996).

Examples of the acid-propagating compound include tert-butyl-2-methyl-2-tosyloxymethyl acetoacetate and 2-phenyl-2-(tosyloxyethyl)-1,3-dioxolane, but are not limited thereto. Of well-known photoacid generators, many of those compounds having poor stability, especially poor thermal stability exhibit an acid-propagating compound-like behavior.

In the resist composition according to the invention, an appropriate amount of the acid-propagating compound is up to 2 parts, and especially up to 1 part by weight per 100 parts by weight of the solids in the composition. Excessive amounts of the acid-propagating compound makes diffusion control difficult, leading to degradation of resolution and pattern configuration.

Component (D)

The basic compound used as component (D) is preferably a compound capable of suppressing the rate of diffusion when the acid generated by the photoacid generator diffuses within the resist film. The inclusion of this type of basic compound holds down the rate of acid diffusion within the resist film, resulting in better resolution. In addition, it suppresses changes in sensitivity following exposure and reduces substrate and environment dependence, as well as improving the exposure latitude and the pattern profile.

Examples of basic compounds include primary, secondary, and tertiary aliphatic amines, mixed amines, aromatic amines, heterocyclic amines, carboxyl group-bearing nitrogenous compounds, sulfonyl group-bearing nitrogenous compounds, hydroxyl group-bearing nitrogenous compounds, hydroxyphenyl group-bearing nitrogenous compounds, alcoholic nitrogenous compounds, amide derivatives, and imide derivatives.

Examples of the basic compound used herein are described in JP-A 2000-194127. Preferred basic compounds are triethylamine, tri-n-propylamine, triisopropylamine, tri-n-butylamine, triisobutylamine, tri-sec-butylamine, tripentylamine, phenethylamine, pyridine, aminopyridine, pyridinium p-toluenesulfonate, monoethanol amine, diethanol amine, triethanol amine, N-ethyldiethanol amine, N,N-diethylethanol amine, triisopropanol amine, 2,2'-iminodiethanol, 2-aminoethanol, 3-amino-1-propanol, 4-amino-1-butanol, 4-(2-hydroxyethyl)morpholine, N,N-dimethylacetamide, tris(2-methoxyethyl)amine, tris(2-ethoxyethyl)amine, tris{2-(methoxymethoxy)ethyl}amine, tris(2-acetyloxyethylamine), and tris(2-propionyloxyethylamine).

The basic compounds may be used alone or in admixture of two or more. The basic compound is preferably formulated in an amount of 0 to 2 parts, and especially 0.01 to 1 part by weight, per 100 parts by weight of the solids in the resist composition. The use of more than 2 parts of the basis compound would result in too low a sensitivity.

Component (E)

Illustrative examples of the organic acid derivatives (E) are described in JP-A 2000-194127, though not limited thereto. Preferred organic acid derivatives include 4-hydroxyphenylacetic acid, 2,5-dihydroxyphenylacetic acid, 3,4-dihydroxyphenylacetic acid, 1,2-phenylenediacetic acid, 1,3-phenylenediacetic acid, 1,4-phenylenediacetic acid, 1,2-phenylenedioxydiacetic acid, 1,4-phenylenedipropanoic acid, benzoic acid, salicylic acid, 4,4-bis(4'-hydroxyphenyl)valeric acid, 4-tert-butoxyphenylacetic acid, 4-(4'-hydroxyphenyl)butyric acid, 3,4-dihydroxymandelic acid, and 4-hydroxymandelic acid. Of these, salicylic acid and 4,4-bis(4'-hydroxyphenyl)valeric acid are preferred. They may be used alone or in admixture of two or more.

In the resist composition comprising the onium salt according to the invention, the organic acid derivative is preferably formulated in an amount of up to 5 parts, and especially up to 1 part by weight, per 100 parts by weight of the solids in the resist composition. The use of more than 5 parts of the organic acid derivative would result in too low a resolution. Depending on the combination of the other components in the resist composition, the organic acid derivative may be omitted.

Component (F)

In one preferred embodiment, the resist composition further contains (F) a compound with a molecular weight of up to 3,000 which changes its solubility in an alkaline developer under the action of an acid, that is, a dissolution inhibitor. Typically, a compound obtained by partially or entirely substituting acid labile substituents on a phenol or carboxylic acid derivative having a molecular weight of up to 2,500 is added as the dissolution inhibitor. Examples of the dissolution inhibitor are described in JP-A 2000-194127, though not limited thereto.

Preferred dissolution inhibitors include 2,2-bis(4'-(2"-tetrahydropyranyloxy))propane, 2,2-bis(4'-tert-butoxycarbonyloxyphenyl)propane, tert-butyl 4,4-bis(4'-(2"-tetrahydropyranyloxy)phenyl)valerate, tert-butyl 4,4-bis (4'-tert-butoxycarbonyloxyphenyl)valerate, and tert-butyl 4,4-bis(4'-tert-butoxycarbonylmethyloxyphenyl)valerate.

In the resist composition comprising the onium salt according to the invention, an appropriate amount of the dissolution inhibitor (F) is up to 20 parts, and especially up to 15 parts by weight per 100 parts by weight of the solids in the composition. With more than 20 parts of the dissolution inhibitor, the resist composition becomes less heat resistant because of an increased content of monomer components.

In a chemical amplification, negative working, resist composition as well, the onium salt of formula (1), (1a), (1a') or (1b) according to the invention may be used as the photoacid generator. This composition further contains an alkali-soluble resin as component (H), examples of which are intermediates of the above-described component (A) though not limited thereto.

Examples of the alkali-soluble resin include poly(p-hydroxystyrene), poly(m-hydroxystyrene), poly(4-hydroxy-2-methylstyrene), poly(4-hydroxy-3-methylstyrene), poly (α-methyl-p-hydroxystyrene), partially hydrogenated p-hydroxystyrene copolymers, p-hydroxystyrene-α-methyl-p-hydroxystyrene copolymers, p-hydroxystyrene-α-methylstyrene copolymers, p-hydroxystyrene-styrene copolymers, p-hydroxystyrene-m-hydroxystyrene copolymers, p-hydroxystyrene-styrene copolymers, p-hydroxystyrene-acrylic acid copolymers, p-hydroxystyrene-methacrylic acid copolymers, p-hydroxystyrene-methyl methacrylate copolymers, p-hydroxystyrene-acrylic acid-methyl methacrylate copolymers, p-hydroxystyrene-methyl acrylate copolymers, p-hydroxy-styrene-methacrylic acid-methyl methacrylate copolymers, poly(methacrylic acid), poly(acrylic acid), acrylic acid-methyl acrylate copolymers, methacrylic acid-methyl methacrylate copolymers, acrylic acid-maleimide copolymers, methacrylic acid-maleimide copolymers, p-hydroxystyrene-acrylic acid-maleimide copolymers, and p-hydroxystyrene-methacrylic acid-maleimide copolymers as well as dendritic and hyperbranched polymers thereof, but are not limited to these combinations.

Preferred are poly(p-hydroxystyrene), partially hydrogenated p-hydroxystyrene copolymers, p-hydroxystyrene-styrene copolymers, p-hydroxystyrene-acrylic acid copolymers, and p-hydroxystyrene-methacrylic acid copolymers, as well as dendritic and hyperbranched polymers of the foregoing polymers.

The polymer should preferably have a weight average molecular weight (Mw) of 3,000 to 100,000. Many polymers with Mw of less than 3,000 do not perform well and are poor in heat resistance and film formation. Many polymers with Mw of more than 100,000 give rise to a problem with respect to dissolution in the resist solvent and developer. The polymer should also preferably have a dispersity (Mw/Mn) of up to 3.5, and more preferably up to 1.5. With a dispersity of more than 3.5, resolution is low in many cases. Although the preparation method is not critical, a poly(p-hydroxystyrene) or similar polymer with a low dispersity or narrow dispersion can be synthesized by living anion polymerization.

To impart a certain function, suitable substituent groups may be introduced into some of the phenolic hydroxyl and carboxyl groups on the acid labile group-protected polymer. Exemplary and preferred are substituent groups for improving adhesion to the substrate, substituent groups for improving etching resistance, and especially substituent groups which are relatively stable against acid and alkali and effective for controlling such that the dissolution rate in an alkali developer of unexposed and low exposed areas of a resist film may not become too high. Illustrative, non-limiting, substituent groups include 2-hydroxyethyl, 2-hydroxypropyl, methoxymethyl, methoxycarbonyl, ethoxycarbonyl, methoxycarbonylmethyl, ethoxycarbonylmethyl, 4-methyl-2-oxo-4-oxolanyl, 4-methyl-2-oxo-4-oxanyl, methyl, ethyl, n-propyl, isopropyl, n-butyl, sec-butyl, acetyl, pivaloyl, adamantyl, isobornyl, and cyclohexyl. It is also possible to introduce acid-decomposable substituent groups such as t-butoxycarbonyl and relatively acid-undecomposable substituent groups such as t-butyl and t-butoxycarbonyl-methyl.

Also contained in the negative resist composition is (I) an acid crosslinking agent capable of forming a crosslinked structure under the action of an acid. Typical acid crosslinking agents are compounds having at least two hydroxymethyl, alkoxymethyl, epoxy or vinyl ether groups in a molecule. Substituted glycoluril derivatives, urea derivatives, and hexa(methoxymethyl)melamine compounds are suitable as the acid crosslinking agent in the chemically amplified, negative resist composition comprising the onium salt according to the invention. Examples include N,N,N',N'-tetramethoxymethylurea, hexamethoxymethylmelamine, tetraalkoxymethyl-substituted glycoluril compounds such as tetrahydroxymethyl-substituted glycoluril and tetramethoxy-methylglycoluril, and condensates of phenolic compounds such as substituted or unsubstituted bis (hydroxymethylphenol) compounds and bisphenol A with epichlorohydrin. Especially preferred acid crosslinking agents are 1,3,5,7-tetraalkoxymethylglycolurils such as 1,3, 5,7-tetramethoxymethylglycoluril, 1,3,5,7-tetrahydroxymethylglycoluril, 2,6-dihydroxymethyl-p-cresol, 2,6-dihydroxymethylphenol, 2,2',6,6'-tetrahydroxymethyl-bisphenol A, 1,4-bis[2-(2-hydroxypropyl)]benzene, N,N,N',N'-tetramethoxymethylurea, and hexamethoxymethylmelamine. In the resist composition, an appropriate amount of the acid crosslinking agent is about 1 to 25 parts, and especially about 5 to 15 parts by weight per 100 parts by weight of the solids in the composition. The acid crosslinking agents may be used alone or in admixture of two or more.

In the chemical amplification type, negative working, resist composition, (J) an alkali-soluble compound having a molecular weight of up to 2,500 may be blended. The compound should preferably have at least two phenol and/or carboxyl groups. Illustrative, non-limiting, examples include cresol, catechol, resorcinol, pyrogallol, fluoroglycin, bis(4-hydroxyphenyl)methane, 2,2-bis(4'-hydroxyphenyl) propane, bis(4-hydroxyphenyl)sulfone, 1,1,1-tris(4'-hydroxyphenyl)ethane, 1,1,2-tris(4'-hydroxy-phenyl)ethane, hydroxybenzophenone, 4-hydroxyphenylacetic acid, 3-hydroxyphenylacetic acid, 2-hydroxyphenylacetic acid, 3-(4-hydroxyphenyl)propionic acid, 3-(2-hydroxyphenyl)-propionic acid, 2,5-dihydroxyphenylacetic acid, 3,4-dihydroxyphenylacetic acid, 1,2-phenylenediacetic acid, 1,3-phenylenediacetic acid, 1,4-phenylenediacetic acid, 1,2-phenylenedioxydiacetic acid, 1,4-phenylenedipropanoic acid, benzoic acid, salicylic acid, 4,4-bis(4'-hydroxyphenyl)-valeric acid, 4-tert-butoxyphenylacetic acid, 4-(4-hydroxyphenyl)butyric acid, 3,4-dihydroxymandelic acid, and 4-hydroxymandelic acid. Of these, salicylic acid and 4,4-bis(4'-hydroxyphenyl)valeric acid are preferred. They may be used alone or in admixture of two or more. The addition amount is 0 to 20 parts, preferably 2 to 10 parts by weight per 100 parts by weight of the solids in the composition although it is not critical.

In the resist composition according to the invention, there may be added such additives as a surfactant for improving coating, and a light absorbing agent for reducing diffuse reflection from the substrate.

Illustrative, non-limiting, examples of the surfactant include nonionic surfactants, for example, polyoxyethylene alkyl ethers such as polyoxyethylene lauryl ether, polyoxyethylene stearyl ether, polyoxyethylene cetyl ether, and polyoxyethylene oleyl ether, polyoxyethylene alkylaryl ethers such as polyoxyethylene octylphenol ether and polyoxyethylene nonylphenol ether, polyoxyethylene polyoxypropylene block copolymers, sorbitan fatty acid esters such as sorbitan monolaurate, sorbitan monopalmitate, and sorbitan monostearate, and polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorochemical surfactants such as EFTOP EF301, EF303 and EF352 (Tohkem Products K.K.), Megaface F171, F172 and F173 (Dai-Nippon Ink & Chemicals K.K.), Florade FC430 and FC431 (Sumitomo 3M K.K.), Asahiguard AG710, Surflon S-381, S-382, SC101, SC102, SC103, SC104, SC105, SC106, Surfynol E1004, KH-10, KH-20, KH-30 and KH-40 (Asahi Glass K.K.); organosiloxane polymers KP341, X-70-092 and X-70-093 (Shin-Etsu Chemical Co., Ltd.), acrylic acid or methacrylic acid Polyflow No. 75 and No. 95 (Kyoeisha Ushi Kagaku Kogyo K.K.). Inter alia, FC430, Surflon S-381 and Surfynol E1004 are preferred. These surfactants may be used alone or in admixture.

In the resist composition according to the invention, the surfactant is preferably formulated in an amount of up to 2 parts, and especially up to 1 part by weight, per 100 parts by weight of the solids in the resist composition.

In the resist composition according to the invention, a UV absorber may be added. Exemplary UV absorbers are described in JP-A 2000-194127, though not limited thereto.

An appropriate amount of UV absorber blended is 0 to 10 parts, more preferably 0.5 to 10 parts, most preferably 1 to 5 parts by weight per 100 parts by weight of the base resin.

For the microfabrication of integrated circuits, any well-known lithography may be used to form a resist pattern from the chemical amplification, positive or negative working, resist composition according to the invention.

The composition is applied onto a substrate (e.g., Si, $SiO_2$, SiN, SiON, TiN, WSi, BPSG, SOG, organic anti-reflecting film, etc.) by a suitable coating technique such as spin coating, roll coating, flow coating, dip coating, spray coating or doctor coating. The coating is prebaked on a hot plate at a temperature of 60 to 150° C. for about 1 to 10 minutes, preferably 80 to 120° C. for 1 to 5 minutes. The resulting resist film is generally 0.1 to 2.0 $\mu$m thick. With a mask having a desired pattern placed above the resist film, the resist film is then exposed to actinic radiation, preferably having an exposure wavelength of up to 300 nm, such as UV, deep-UV, electron beams, x-rays, excimer laser light, $\gamma$-rays and synchrotron radiation in an exposure dose of about 1 to 200 $mJ/cm^2$, preferably about 10 to 100 $mJ/cm^2$. The film is further baked on a hot plate at 60 to 150° C. for 1 to 5 minutes, preferably 80 to 120° C. for 1 to 3 minutes (post-exposure baking=PEB).

Thereafter the resist film is developed with a developer in the form of an aqueous base solution, for example, 0.1 to 5%, preferably 2 to 3% aqueous solution of tetramethylammonium hydroxide (TMAH) for 0.1 to 3 minutes, preferably 0.5 to 2 minutes by conventional techniques such as dipping, puddling or spraying. In this way, a desired resist pattern is formed on the substrate. It is appreciated that the resist composition of the invention is best suited for micropatterning using such actinic radiation as deep UV with a wavelength of 254 to 193 nm, electron beams, x-rays, excimer laser light, $\gamma$-rays and synchrotron radiation. With any of the above-described parameters outside the above-described range, the process may sometimes fail to produce the desired pattern.

EXAMPLE

Examples of the invention are given below by way of illustration and not by way of limitation.

Synthesis Example 1
Synthesis of sodium 3-methoxy-4-(4'-methylphenylsulfonyl-oxy)benzenesulfonate In 80 g of tetrahydrofuran and 65 g of water were dissolved 50 g (0.2 mol) of potassium guaiacolsulfonate hydrate and 38 g (0.2 mol) of p-toluenesulfonyl chloride. With stirring under ice cooling, an aqueous sodium hydroxide solution (containing 8 g (0.2 mol) of sodium hydroxide in 15 g of water) was added dropwise at a temperature below 20° C. After the completion of dropwise addition, the reaction solution was ripened for 2 hours at room temperature. Dichloromethane, 200 g, was added to the reaction solution whereupon sodium 3-methoxy-4-(4'-methylphenylsulfonyloxy)benzenesulfonate crystallized. The crystals were collected by filtration and washed with 200 g of dichloromethane. The yield was 90 g (wet).

The crystal thus obtained could be a mixture of sodium salt and potassium salt. Since they could be removed as sodium ions and potassium ions by anion exchange in the subsequent step, the product was used in the subsequent reaction without purification.

Synthesis Example 2
Synthesis of triphenylsulfonium chloride

In 400 g of dichloromethane was dissolved 40 g (0.2 mol) of diphenyl sulfoxide. With stirring under ice cooling, 65 g (0.6 mol) of trimethylsilyl chloride was added dropwise at a temperature below 20° C. The reaction solution was ripened at the temperature for 30 minutes. Then, the Grignard reagent which was separately prepared from 14.6 g (0.6 mol) of metallic magnesium, 67.5 g (0.6 mol) of chlorobenzene and 168 g of THF was added dropwise at a temperature below 20° C. The reaction solution was ripened for one hour. At a temperature below 20° C., 50 g of water was added to the reaction solution for terminating the reaction. Further, 150 g of water, 10 g of 12N hydrochloric acid and 200 g of diethyl ether were added to the solution.

The aqueous layer was separated and washed with 100 g of diethyl ether, obtaining an aqueous solution of triphenylsulfonium chloride. This aqueous solution was subject to the subsequent reaction without further isolation.

Synthesis Example 3

Synthesis of 4-tert-butylphenyldiphenylsulfonium Chloride

The end compound was synthesized as in Synthesis Example 2 except that 4-tert-butylchlorobenzene was used instead of the chlorobenzene in Synthesis Example 2 and the quantity of water for extraction was increased.

Synthesis Example 4

Synthesis of 4-tert-butoxyphenyldiphenylsulfonium Chloride

The end compound was synthesized as in Synthesis Example 2 except that 4-tert-butoxychlorobenzene was used instead of the chlorobenzene in Synthesis Example 2, dichloromethane containing 5% by weight of triethylamine was used as the solvent, and the quantity of water for extraction was increased.

Synthesis Example 5

Synthesis of tris(4-methylphenyl)sulfonium Chloride

The end compound was synthesized as in Synthesis Example 2 except that bis(4-methylphenyl) sulfoxide was used instead of the phenyl sulfoxide in Synthesis Example 2, 4-chlorotoluene was used instead of the chlorobenzene, and the quantity of water for extraction was increased.

Synthesis Example 6

Synthesis of tris(4-tert-butylphenyl)sulfonium chloride

The end compound was synthesized as in Synthesis Example 2 except that bis(4-tert-butylphenyl) sulfoxide was used instead of the phenyl sulfoxide in Synthesis Example 2, 4-tert-butylchlorobenzene was used instead of the chlorobenzene, and the quantity of water for extraction was increased.

Synthesis Example 7

Synthesis of bis(4-tert-butylphenyl)iodonium hydrogensulfate

A mixture of 84 g (0.5 mol) of tert-butylbenzene, 53 g (0.25 mol) of potassium iodate and 50 g of acetic anhydride was stirred under ice cooling, and a mixture of 35 g of acetic anhydride and 95 g of conc. sulfuric acid was added dropwise thereto at a temperature below 30° C. The reaction mixture was ripened for 3 hours at room temperature and cooled with ice again, after which 250 g of water was added dropwise for terminating the reaction. The reaction solution was extracted with 400 g of dichloromethane. To the organic layer, 6 g of sodium hydrogensulfite was added for decoloring. The organic layer was washed with 250 g of water three times. After washing, the organic layer was concentrated in vacuum, obtaining the crude end product. The product was used in the subsequent reaction without further purification.

Synthesis Example 8

Synthesis of triphenylsulfonium 3-methoxy-4-(4'-methylphenylsulfonyloxy)benzenesulfonate The sodium 3-methoxy-4-(4'-methylphenylsulfonyloxy)benzenesulfonate crude product obtained in Synthesis Example 1, 90 g, was added to the aqueous triphenylsulfonium chloride solution obtained in Synthesis Example 2 and 400 g of dichloromethane, which was stirred for one hour at room temperature. The organic layer was separated, washed with 400 g of water, and concentrated in vacuum. The residue, 150 g, was purified by silica gel column chromatography (eluent, dichloromethane/methanol), obtaining the end product, triphenylsulfonium 3-methoxy-4-(4'-methylphenyl-sulfonyloxy)benzenesulfonate as an oily matter in an amount of 69 g (yield 56%).

The triphenylsulfonium 3-methoxy-4-(4'-methylphenyl-sulfonyloxy)benzenesulfonate thus obtained was analyzed by nuclear magnetic resonance (NMR) spectroscopy and infrared (IR) absorption spectroscopy, with the results shown below.

$^1$H-NMR: CDCl$_3$, ppm

| (1) | Ha | 2.40 | singlet | 3H |
|---|---|---|---|---|
| (2) | Hb | 7.23–7.25 | doublet | 2H |
| (3) | Hd | 3.45 | singlet | 3H |
| (4) | He | 7.40–7.41 | doublet | 1H |
| (5) | Hf | 7.00–7.03 | doublet | 1H |
| (6) | Hg | 7.35–7.38 | quadruplet | 1H |
| (7) | Hc, Hh | 7.61–7.75 | multiplet | 17H |

IR: cm$^{-1}$ 3087, 3062, 1728, 1635, 1597, 1493, 1477, 1448, 1398, 1371, 1265, 1198, 1163, 1090, 1041, 1020, 997, 895, 841, 752, 721, 683, 636, 609

Synthesis Example 9

Synthesis of 4-tert-butylphenyldiphenylsulfonium 3-methoxy-4-(4'-methylphenylsulfonyloxy)benzenesulfonate The end compound was synthesized as in Synthesis Example 8 except that the 4-tert-butylphenyldiphenylsulfonium chloride in Synthesis Example 3 was used instead of the aqueous triphenylsulfonium chloride solution in Synthesis Example 2.

Synthesis Example 10

Synthesis of 4-tert-butoxyphenyldiphenylsulfonium 3-methoxy-4-(4'-methylphenylsulfonyloxy)benzenesulfonate The end compound was synthesized as in Synthesis Example 8 except that the 4-tert-butoxyphenyldiphenylsulfonium chloride in Synthesis Example 4 was used instead of the aqueous triphenylsulfonium chloride solution in Synthesis Example 2.

Synthesis Example 11

Synthesis of tris(4-methylphenyl)sulfonium 3-methoxy-4-(4'-methylphenylsulfonyloxy)benzenesulfonate The end compound was synthesized as in Synthesis Example 8 except that the tris(4-methylphenyl)sulfonium chloride in Synthesis Example 5 was used instead of the aqueous triphenylsulfonium chloride solution in Synthesis Example 2.

The tris(4-methylphenyl)sulfonium 3-methoxy-4-(4'-methylphenylsulfonyloxy)benzenesulfonate thus obtained was analyzed by $^1$H-NMR, IR spectroscopy, and elemental analysis, with the results shown below.

$^1$H-NMR: CDCl$_3$, ppm

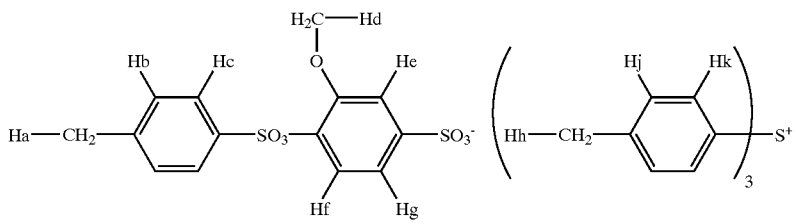

| (1) | Ha | 2.39 | singlet | 3H |
| --- | --- | --- | --- | --- |
| (2) | Hb | 7.21–7.24 | doublet | 2H |
| (4) | Hc | 7.63–7.66 | doublet | 2H |
| (5) | Hd | 3.44 | singlet | 3H |
| (6) | Hf | 7.01–7.03 | doublet | 1H |
| (7) | He, Hg, Hi | 7.39–7.44 | multiplet | 8H |
| (8) | Hh | 2.42 | singlet | 9H |
| (9) | Hj | 7.54–7.58 | doublet | 6H |

IR: cm$^{-1}$ 3037, 2966, 1591, 1493, 1446, 1398, 1371, 1296, 1263, 1207, 1167, 1119, 1088, 1039, 1020, 895, 843, 812, 748, 723, 702, 681, 660, 640, 609

Elemental analysis: $C_{35}H_{34}O_7S_3$ (%). Calcd. C 63.4H 5.2. Found C 64.3H 5.2.

Synthesis Example 12

Synthesis of tris(4-tert-butylphenyl)sulfonium 3-methoxy-4-(4'-methylphenylsulfonyloxy)benzenesulfonate The end compound was synthesized as in Synthesis Example 8 except that the tris(4-tert-butylphenyl)sulfonium chloride in Synthesis Example 6 was used instead of the aqueous triphenylsulfonium chloride solution in Synthesis Example 2.

The tris(4-tert-butylphenyl)sulfonium 3-methoxy-4-(4'-methylphenylsulfonyloxy)benzenesulfonate thus obtained was analyzed by $^1$H-NMR, IR spectroscopy, and elemental analysis, with the results shown below.

$^1$H-NMR: CDCl$_3$, ppm

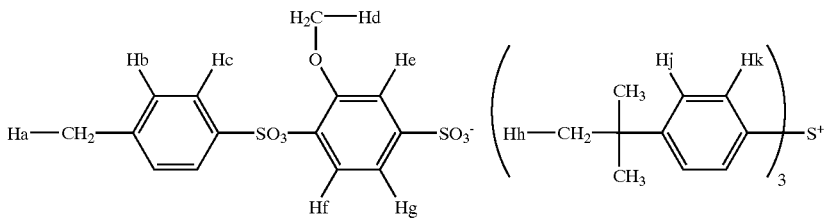

| (1) | Ha | 2.39 | singlet | 3H |
| --- | --- | --- | --- | --- |
| (2) | Hb | 7.21–7.24 | doublet | 2H |
| (4) | Hd | 3.44 | singlet | 3H |
| (5) | He | 7.46–7.47 | doublet | 1H |
| (6) | Hf | 7.03–7.06 | doublet | 1H |
| (7) | Hg | 7.42–7.45 | quadruplet | 1H |
| (8) | Hh | 2.42 | singlet | 27H |
| (9) | Hc, Hi, Hj | 7.62–7.70 | multiplet | 14H |

IR: cm$^{-1}$ 3058, 2964, 2906, 2869, 1589, 1491, 1464, 1400, 1369, 1265, 1232, 1198, 1163, 1103, 1090, 1072, 1043, 1022, 894, 839, 752, 719, 683, 656, 632, 609

Elemental analysis: $C_{44}H_{52}O_7S_3$ (%). Calcd. C 67.0H 6.6. Found C 68.1H 6.2.

Synthesis Example 13

Synthesis of bis(4-tert-butylphenyl)iodonium 3-methoxy-4-(4'-methylphenylsulfonyloxy)benzenesulfonate The end compound was synthesized as in Synthesis Example 8 except that the bis(4-tert-butylphenyl)iodonium hydrogensulfate in Synthesis Example 7 was used instead of the aqueous triphenylsulfonium chloride solution in Synthesis Example 2, and 200 g of water was used.

Synthesis Example 14

Synthesis of tris(4-tert-butylphenyl)sulfonium 3-methoxy-4-(phenylsulfonyloxy)benzenesulfonate Sodium 3-methoxy-4-(phenylsulfonyloxy)benzenesulfonate was prepared as in Synthesis Example 1 except that benzenesulfonyl chloride was used instead of the 4-toluenesulfonic acid chloride in Synthesis Example 1. The end compound was then synthesized as in Synthesis Example 12.

Synthesis Example 15

Synthesis of triphenylsulfonium 3-methoxy-4-(2-naphthylsulfonyloxy)benzenesulfonate Sodium 3-methoxy-4-(2-naphthylsulfonyloxy)benzenesulfonate was prepared as in Synthesis Example 1 except that 2-naphthylsulfonyl chloride was used instead of the 4-toluenesulfonic acid chloride in Synthesis Example 1. The end compound was then synthesized as in Synthesis Example 8.

For further reference, the synthesis of branched polymers is described below.

Reference Example 1

Synthesis of tri-branched poly(p-hydroxystyrene)

A 1-liter flask was charged with 500 ml of tetrahydrofuran as a solvent and 0.01 mol of sec-butyl lithium as an initiator. To the solution at −78° C. was added 40 g of p-tert-butoxystyrene. With stirring, polymerization reaction was effected for 30 minutes. The reaction solution turned red. For producing a branched polymer, 0.005 mol of p-chloromethylstyrene was added to the reaction solution whereupon reaction was effected for 5 minutes. The reaction solution was red. Further 20 g of p-tert-butoxystyrene was added. With stirring, polymerization reaction was effected for 30 minutes. Polymerization was stopped by adding 0.1 mol of methanol to the reaction solution.

For purifying the polymer, the reaction mixture was poured into methanol whereupon the polymer precipitated. Separation and drying yielded 44 g of a white polymer which was tri-branched poly(p-tert-butoxystyrene).

For producing tri-branched poly(p-hydroxystyrene), 44 g of the above tri-branched poly(p-tert-butoxystyrene) was dissolved in 400 ml of acetone. A minor amount of conc. hydrochloric acid was added to the solution at 60° C., which was stirred for 7 hours. The reaction solution was poured into water whereupon the polymer precipitated. Washing and drying yielded 25 g of a white polymer. Since a peak attributable to tert-butyl group was not found in GPC and proton-NMR analysis, this polymer was confirmed to be tri-branched poly(p-hydroxystyrene) having a narrow molecular weight distribution.

The polymer had a weight average molecular weight (Mw) of 8,500 as determined by GPC using polystyrene standard and a dispersity (Mw/Mn) of 1.10.

Reference Example 2
Synthesis of nona-branched poly(p-hydroxystyrene)

A 2-liter flask was charged with 1000 ml of tetrahydrofuran as a solvent and 0.06 mol of sec-butyl lithium as an initiator. To the solution at −78° C. was added 60 g of p-tert-butoxystyrene. With stirring, polymerization reaction was effected for 30 minutes. The reaction solution turned red. For producing a tri-branched polymer, 0.03 mol of p-chloromethylstyrene was added to the reaction solution whereupon reaction was effected for 5 minutes. Then 30 g of p-tert-butoxystyrene was added to the reaction solution, which was stirred for 30 minutes for polymerization. The reaction solution was red. For producing penta-branched polymer, 0.015 mol of p-chloromethylstyrene was added to the reaction solution whereupon reaction was effected for 5 minutes. Then 15 g of p-tert-butoxystyrene was added to the reaction solution, which was stirred for 30 minutes for polymerization. The reaction solution was red. Finally for producing nona-branched polymer, 0.0075 mol of p-chloromethylstyrene was added to the reaction solution whereupon reaction was effected for 5 minutes. Then 7.5 g of p-tert-butoxystyrene was added to the reaction solution, which was stirred for 30 minutes for polymerization. The reaction solution was red. Polymerization was stopped by adding 0.1 mol of carbon dioxide gas to the reaction solution.

For purifying the polymer, the reaction mixture was poured into methanol whereupon the polymer precipitated. Separation and drying yielded 99 g of a white polymer which was nona-branched poly(p-tert-butoxystyrene).

For converting to nona-branched poly(p-hydroxystyrene), 99 g of the above nona-branched poly(p-tert-butoxystyrene) was dissolved in 1000 ml of acetone. A minor amount of conc. hydrochloric acid was added to the solution at 60° C., which was stirred for 7 hours. The reaction solution was poured into water whereupon the polymer precipitated. Washing and drying yielded 66 g of a white polymer. Since a peak attributable to tert-butyl group was not found on GPC and proton-NMR analysis, this polymer was confirmed to be nona-branched poly(p-hydroxystyrene) having a narrow molecular weight distribution.

The polymer had a weight average molecular weight (Mw) of 11,000 as determined by GPC using polystyrene standard and a dispersity (Mw/Mn) of 1.25.

Examples 1–24 and Comparative Examples 1–3

Resist materials were prepared in accordance with the formulation shown in Tables 1 to 3. The components used are shown below.

Polymer A: poly(p-hydroxystyrene) in which hydroxyl groups are protected with 15 mol % of 1-ethoxyethyl groups and 15 mol % of tert-butoxycarbonyl groups, having a weight average molecular weight of 12,000.

Polymer B: poly(p-hydroxystyrene) in which hydroxyl groups are protected with 10 mol % of 1-ethoxyethyl groups and 15 mol % of tert-butoxycarbonyl groups, having a weight average molecular weight of 11,000.

Polymer C: nano-branched poly(p-hydroxystyrene) in which hydroxyl groups are protected with 20 mol % of 1-ethoxyethyl groups and 5 mol % of tert-butoxycarbonyl groups, having a weight average molecular weight of 14,000.

Polymer D: poly(p-hydroxystyrene) in which hydroxyl groups are protected with 25 mol % of 1-ethoxyethyl groups and crosslinked with 3 mol % of 1,2-propane diol divinyl ether, having a weight average molecular weight of 13,000.

Polymer E: tri-branched poly(p-hydroxystyrene) in which hydroxyl groups are protected with 30 mol % of 1-ethoxyethyl groups, having a weight average molecular weight of 11,000.

Polymer F: poly(p-hydroxystyrene) in which hydroxyl groups are protected with 10 mol % of 1-ethoxyethyl groups and 3 mol % of tert-butoxycarbonyl groups and crosslinked with 3 mol % of 1,2-propane diol divinyl ether, having a weight average molecular weight of 15,000.

Polymer G: poly(p-hydroxystyrene) in which hydroxyl groups are protected with 15 mol % of 1-ethoxyethyl groups and 10 mol % of tert-butoxycarbonyl groups and crosslinked with 3 mol % of 1,2-propane diol divinyl ether, having a weight average molecular weight of 13,000.

Polymer H: p-hydroxystyrene/1-ethylcyclopentyl methacrylate copolymer having a compositional ratio (molar ratio) of 70:30, and having a weight average molecular weight of 11,000.

Polymer I: p-hydroxystyrene/1-ethylcyclopentyl acrylate copolymer having a compositional ratio (molar ratio) of 65:35, and having a weight average molecular weight of 14,000.

Polymer J: the same as Polymer G further containing 5% by weight of styrene and having a weight average molecular weight of 12,000.

Polymer K: p-hydroxystyrene/1-ethylcyclopentyl methacrylate copolymer having a compositional ratio (molar ratio) of 70:30, phenolic hydroxyl groups in the p-hydroxystyrene being crosslinked with 2 mol % of 1,2-propane diol divinyl ether, the copolymer having a weight average molecular weight of 13,000.

Polymer L: p-hydroxystyrene/1-ethylcyclopentyl methacrylate/p-tert-butoxystyrene copolymer having a compositional ratio (molar ratio) of 60:30:10, and having a weight average molecular weight of 12,000.

Polymer M: p-hydroxystyrene/1-ethylcyclopentyl methacrylate/tert-butoxycarbonyloxystyrene copolymer having a compositional ratio (molar ratio) of 70:20:10, phenolic hydroxyl groups in the p-hydroxystyrene being crosslinked with 1 mol % of 1,2-propane diol divinyl ether, the copolymer having a weight average molecular weight of 12,000.

Polymer N: poly(p-hydroxystyrene) in which hydroxyl groups are protected with 8 mol % of acetyl groups, having a weight average molecular weight of 8,000.

PAG1: triphenylsulfonium 3-methoxy-4-(4'-methylphenyl-sulfonyloxy)benzenesulfonate
PAG2: 4-tert-butoxyphenyldiphenylsulfonium 3-methoxy-4-(4'-methylphenylsulfonyloxy)benzenesulfonate
PAG3: bis(4-tert-butylphenyl)iodonium 3-methoxy-4-(4'-methylphenylsulfonyloxy)benzenesulfonate
PAG4: (4-tert-butoxyphenyl)diphenylsulfonium p-toluene-sulfonate
PAG5: (4-tert-butoxyphenyl)diphenylsulfonium 10-camphor-sulfonate
PAG6: bis(tert-butylsulfonyl)diazomethane
PAG7: bis(cyclohexylsulfonyl)diazomethane
PAG8: bis(2,4-dimethylphenylsulfonyl)diazomethane
PAG9: N-10-camphorsulfonyloxysuccinimide
Crosslinker A: 1,3,5,7-tetramethoxymethylglycoluril
Dissolution inhibitor A: bis(4-tert-butoxycarbonyloxy-phenyl)methane
Basic compound A: tri-n-butylamine
Basic compound B: tris(2-methoxyethyl)amine
Organic acid derivative A: 4,4-bis(4'-hydroxyphenyl) valeric acid
Organic acid derivative B: salicylic acid
Surfactant A: FC-430 (Sumitomo 3M K.K.)
Surfactant B: Surflon S-381 (Asahi Glass K.K.)
UV absorber A: 9,10-dimethylanthracene
Solvent A: propylene glycol methyl ether acetate
Solvent B: ethyl lactate

TABLE 1

| Composition (pbw) | Example 1 | 2 | 3 | 4 | 5 | 6 | 7 | 8 | 9 | 10 | 11 | 12 |
|---|---|---|---|---|---|---|---|---|---|---|---|---|
| Polymer A | 80 | | | | | | | | | | 40 | 40 |
| Polymer B | | 80 | | | | | | | | | | |
| Polymer C | | | 80 | | | | | | | | | |
| Polymer D | | | | 80 | | | | | | | 40 | |
| Polymer E | | | | | 80 | | | | | | | |
| Polymer F | | | | | | 80 | | | | | | |
| Polymer G | | | | | | | 80 | | | | | 40 |
| Polymer H | | | | | | | | 80 | | | | |
| Polymer I | | | | | | | | | 80 | | | |
| Polymer J | | | | | | | | | | 80 | | |
| Polymer K | | | | | | | | | | | | |
| Polymer L | | | | | | | | | | | | |
| Polymer M | | | | | | | | | | | | |
| Polymer N | | | | | | | | | | | | |
| PAG1 | 2 | | | 2 | | 2 | 1 | 2 | | | 2 | 1 |
| PAG2 | | 2 | | | 1 | | | | 2 | | | |
| PAG3 | | | 2 | | 1 | | | | | 2 | | |
| PAG4 | 1 | | | | | | 1 | | | | | |
| PAG5 | | 2 | | | 1 | | | 2 | 2 | 2 | | |
| PAG6 | | | 2 | | | | | | | 0.5 | 1 | 1 |
| PAG7 | | | | | | | 2 | 0.5 | | | | |
| PAG8 | | | | 1 | | | | | | 0.25 | | 2 |
| PAG9 | | | | | 0.5 | | | | | | | |
| Crosslinker A | | | | | | | | | | | | |
| Dissolution inhibitor A | | | | | | | | | | | | |
| Basic compound A | 0.125 | 0.125 | | | 0.125 | 0.06 | 0.125 | 0.125 | 0.1 | 0.125 | | |
| Basic compound B | | | 0.125 | 0.125 | | 0.06 | | | 0.025 | | 0.125 | 0.125 |
| Organic acid derivative A | 1 | 1 | 1 | | 1 | 1 | 1 | 0.25 | 1 | 1 | 1 | 1 |
| Organic acid derivative B | | | | 0.5 | | | | 0.25 | | | | |
| Surfactant A | 0.25 | 0.25 | | | | 0.25 | 0.25 | 0.25 | | 0.25 | 0.25 | 0.25 |
| Surfactant B | | | 0.25 | 0.25 | 0.25 | | | | 0.25 | | | |
| UV absorber A | | | | | | | | | | | | |
| Solvent A | 280 | 280 | 388 | 280 | 388 | 280 | 280 | 280 | 280 | 388 | 280 | 280 |
| Solvent B | 105 | 105 | | 105 | | 105 | 105 | 105 | 105 | | 105 | 105 |

TABLE 2

| Composition (pbw) | Example 13 | 14 | 15 | 16 | 17 | 18 | 19 | 20 | 21 | 22 | 23 | 24 |
|---|---|---|---|---|---|---|---|---|---|---|---|---|
| Polymer A | 40 | 50 | 50 | 50 | | | | | | | | |
| Polymer B | | | | | | | | | | | | |
| Polymer C | | | | | | | | | | | | |
| Polymer D | | 20 | 20 | 10 | 40 | 40 | 50 | | | | | |
| Polymer E | | | | | | | | | | | | |
| Polymer F | | | | | | | | | | | | |
| Polymer G | | 10 | | 10 | 40 | | 20 | | | | | |

TABLE 2-continued

| Composition (pbw) | Example 13 | 14 | 15 | 16 | 17 | 18 | 19 | 20 | 21 | 22 | 23 | 24 |
|---|---|---|---|---|---|---|---|---|---|---|---|---|
| Polymer H | | | | | | | | 40 | | | | |
| Polymer I | 40 | | 10 | 10 | | 40 | 10 | | | | | |
| Polymer J | | | | | | | | | | | 40 | |
| Polymer K | | | | | | | | | 80 | | 40 | |
| Polymer L | | | | | | | 40 | | | | | |
| Polymer M | | | | | | | | | | 80 | | |
| Polymer N | | | | | | | | | | | | 80 |
| PAG1 | 2 | 1 | | 1 | 2 | 2 | | | | | | |
| PAG2 | | 1 | | | | | 1 | | 2 | | | |
| PAG3 | | | 2 | | | | 1 | 2 | | 2 | 2 | 4 |
| PAG4 | | 1 | 1 | 1 | | | 1 | | | | | |
| PAG5 | | | 1 | | 1 | 1 | | 2 | 2 | 2 | 1 | |
| PAG6 | 1 | | | 1 | 1 | | | 0.5 | | | | 1 |
| PAG7 | | | | | | 1 | | | | 0.25 | 0.5 | |
| PAG8 | | | | | | | | 0.5 | | | | |
| PAG9 | | | | | | | | | 0.5 | | | |
| Crosslinker A | | | | | | | | | | | | 10 |
| Dissolution inhibitor A | | 2 | 2 | | | | | | | | | |
| Basic compound A | 0.125 | | | 0.075 | 0.125 | 0.125 | | 0.125 | | | | |
| Basic compound B | | 0.125 | 0.125 | 0.05 | | | 0.125 | | 0.125 | 0.125 | 0.125 | 0.125 |
| Organic acid derivative A | 1 | | | | | | 1 | | 0.5 | | | |
| Organic acid derivative B | | 1 | 1 | 0.5 | 1 | 0.5 | | 1 | | 0.5 | 1 | |
| Surfactant A | 0.25 | | | 0.125 | 0.25 | 0.25 | | 0.25 | 0.25 | 0.125 | | |
| Surfactant B | | 0.25 | 0.25 | 0.125 | | | 0.25 | | | 0.125 | 0.25 | 0.25 |
| UV absorber A | | | | 0.25 | | | | | | | | |
| Solvent A | 280 | 388 | 388 | 388 | 280 | 280 | 388 | 388 | 280 | 280 | 388 | 388 |
| Solvent B | 105 | | | | 105 | 105 | | | 105 | 105 | | |

TABLE 3

| Composition (pbw) | Comparative Example 1 | 2 | 3 |
|---|---|---|---|
| Polymer A | 80 | | |
| Polymer D | | 80 | |
| Polymer G | | | 80 |
| PAG4 | | | 1 |
| PAG8 | 2 | | 2 |
| PAG9 | 1 | 2 | |
| Organic acid derivative A | | | |
| Organic acid derivative B | 1 | | |
| Basic compound A | 0.125 | 0.125 | |
| Basic compound B | | | 0.125 |
| Surfactant A | 0.25 | 0.25 | |
| Surfactant B | | | 0.25 |
| Solvent A | 388 | 388 | 388 |

The resist materials thus obtained were each filtered through a 0.2-μm Teflon® filter, thereby giving resist solutions. These resist solutions were spin-coated onto silicon wafers, then baked at 100° C. for 90 seconds on a hot plate to give resist films having a thickness of 0.6 μm. The resist films were exposed using an excimer laser scanner NSR2005EX (Nikon Corp., NA 0.5), then baked (PEB) at 110° C. for 90 seconds, and developed with a solution of 2.38% tetramethylammonium hydroxide in water, thereby giving positive patterns (Examples 1 to 23 and Comparative Examples 1–3) or negative patterns (Example 24).

The resulting resist patterns were evaluated as described below.

Resist Pattern Evaluation

The exposure dose which provided a 1:1 resolution at the top and bottom of a 0.24-μm line-and-space pattern was the optimum exposure dose (sensitivity Eop). The minimum line width of a line-and-space pattern which was ascertained separate at this dose was the resolution of a test resist. The shape in cross section of the resolved resist pattern was examined under a scanning electron microscope.

The PED stability of a resist was evaluated by effecting post-exposure bake (PEB) after 24 hours of holding from exposure at the optimum dose and determining a variation in line width (or groove width for the negative resist). The less the variation, the greater is the PED stability.

The results of resist pattern evaluation are shown in Table 4.

Other Evaluation

The solubility of resist material in a solvent mixture was examined by visual observation and in terms of clogging upon filtration.

With respect to the applicability of a resist solution, uneven coating was visually observed. Additionally, using a film gage Clean Track Mark 8 (Tokyo Electron K.K.), the thickness of a resist film on a common wafer was measured at different positions, based on which a variation from the desired coating thickness (0.6 μm) was calculated. The applicability was rated "good" when the variation was within 0.5% (that is, within 0.003 μm), "unacceptable" when the variation was from more than 0.5% to 1%, and "poor" when the variation was more than 1%.

Storage stability was judged in terms of foreign matter precipitation or sensitivity change during aging. After the resist solution was aged for 100 days at the longest, the number of particles of greater than 0.3 μm per ml of the resist solution was counted by means of a particle counter KL-20A (Rion K.K.), and the foreign matter precipitation was determined "good" when the number of particles is not more than 5. Also, the sensitivity change was rated "good" when a change with time of sensitivity (Eop) was within 5% from that immediately after preparation, and "poor" when the change is more than 5%.

Debris appearing on the developed pattern was observed under a scanning electron microscope (TDSEM) model S-7280H (Hitachi Ltd.). The resist film was rated "good" when the number of foreign particles was up to 10 per 100 $\mu m^2$, "unacceptable" when from 11 to 15, and "poor" when more than 15.

Debris left after resist peeling was examined using a surface scanner Surf-Scan 6220 (Tencol Instruments). A resist-coated 8-inch wafer was subjected to entire exposure rather than patterned exposure, processed in a conventional manner, and developed with a 2.38% TMAH solution before the resist film was peeled off (only the resist film in the exposed area was peeled). After the resist film was peeled, the wafer was examined and rated "good" when the number of foreign particles of greater than 0.20 $\mu m$ was up to 100, "unacceptable" when from 101 to 150, and "poor" when more than 150.

The results are shown in Table 5.

TABLE 4

|  | Sensitivity (mJ/cm$^2$) | Resolution ($\mu m$) | Profile | 24 hr PED dimensional stability (nm) |
|---|---|---|---|---|
| Example 1 | 26 | 0.21 | rectangular | −8 |
| Example 2 | 27 | 0.20 | rectangular | −10 |
| Example 3 | 26 | 0.19 | rectangular | −8 |
| Example 4 | 29 | 0.20 | rectangular | −10 |
| Example 5 | 28 | 0.19 | rectangular | −9 |
| Example 6 | 23 | 0.19 | rectangular | −9 |
| Example 7 | 25 | 0.20 | rectangular | −9 |
| Example 8 | 26 | 0.20 | rectangular | −11 |
| Example 9 | 27 | 0.20 | rectangular | −5 |
| Example 10 | 28 | 0.20 | rectangular | 8 |
| Example 11 | 28 | 0.20 | rectangular | −7 |
| Example 12 | 27 | 0.20 | rectangular | −7 |
| Example 13 | 26 | 0.19 | rectangular | 5 |
| Example 14 | 29 | 0.20 | rectangular | −10 |
| Example 15 | 28 | 0.20 | rectangular | −6 |
| Example 16 | 28 | 0.20 | rectangular | −5 |
| Example 17 | 27 | 0.20 | rectangular | −10 |
| Example 18 | 26 | 0.19 | rectangular | 5 |
| Example 19 | 27 | 0.20 | rectangular | −5 |
| Example 20 | 26 | 0.19 | rectangular | 5 |
| Example 21 | 26 | 0.21 | rectangular | −5 |
| Example 22 | 29 | 0.20 | rectangular | 8 |
| Example 23 | 24 | 0.19 | rectangular | 10 |
| Example 24 | 26 | 0.21 | rectangular (negative) | 5 |
| Comparative Example 1 | 35 | 0.22 | forward tapered | −30 |
| Comparative Example 2 | 34 | 0.23 | rounded head | −30 |
| Comparative Example 3 | 34 | 0.23 | forward tapered | 30 |

TABLE 5

|  | Dissolution | Application | 100 day storage stability | Debris after development (patterning) | Debris after peeling |
|---|---|---|---|---|---|
| Example 1 | good | good | good | good | good |
| Example 2 | good | good | good | good | good |
| Example 3 | good | good | good | good | good |
| Example 4 | good | good | good | good | good |
| Example 5 | good | good | good | good | good |
| Example 6 | good | good | good | good | good |
| Example 7 | good | good | good | good | good |
| Example 8 | good | good | good | good | good |
| Example 9 | good | good | good | good | good |
| Example 10 | good | good | good | good | good |
| Example 11 | good | good | good | good | good |
| Example 12 | good | good | good | good | good |
| Example 13 | good | good | good | good | good |
| Example 14 | good | good | good | good | good |
| Example 15 | good | good | good | good | good |
| Example 16 | good | good | good | good | good |
| Example 17 | good | good | good | good | good |
| Example 18 | good | good | good | good | good |
| Example 19 | good | good | good | good | good |
| Example 20 | good | good | good | good | good |
| Example 21 | good | good | good | good | good |
| Example 22 | good | good | good | good | good |
| Example 23 | good | good | good | good | good |
| Example 24 | good | good | good | good | good |
| Comparative Example 1 | good | good | <30 days (sensitivity changed) | poor | poor |
| Comparative Example 2 | good | good | <30 days (sensitivity changed) | good | unacceptable |
| Comparative Example 3 | unacceptable | good | good | poor | poor |

There have been described specific onium salts having an arylsulfonyloxybenzenesulfonate anion. Since the benzenesulfonate anion of the onium salt has a sulfonate group incorporated therein, chemical amplification type resist compositions comprising the onium salts as the photoacid generator have many advantages including improved resolution, improved focus latitude, minimized line width variation or shape degradation even on long-term PED, minimized debris left after coating, development and peeling, and improved pattern profile after development. Because of high resolution, the compositions are suited for microfabrication, especially by deep UV lithography.

Japanese Patent Application No. 2000-322182 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:
1. An onium salt of the following general formula (1):

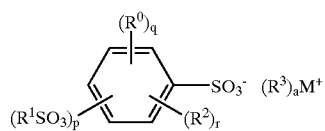

(1)

wherein $R^1$ is a substituted or unsubstituted aryl group of 6 to 14 carbon atoms, $R^2$ which may be the same or different is hydrogen or a substituted or unsubstituted, straight, branched or cyclic alkyl group of 1 to 6 carbon atoms, $R^0$ is a hydroxyl, alkoxy, halogen or nitro group, p, q and r each are 1 or 2, $R^3$ which may be the same or different is a substituted or unsubstituted, straight, branched or cyclic alkyl group of 1 to 10 carbon atoms or substituted or unsubstituted aryl group of 6 to 14 carbon atoms, M is a sulfur or iodine atom, and "a" is equal to 3 when M is sulfur and equal to 2 when M is iodine.

2. A sulfonium salt of the following general formula (1a):

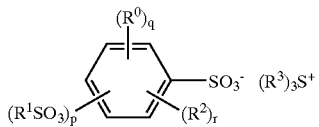
(1a)

wherein $R^1$, $R^2$, $R^0$, p, q, r and $R^3$ are as defined in claim 1.

3. A sulfonium salt of the following general formula (1a'):

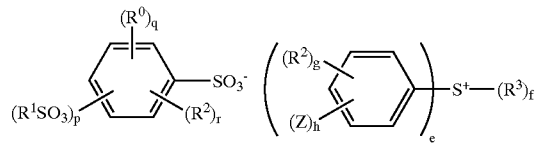
(1a')

wherein $R^1$, $R^2$, $R^0$, p, q, r and $R^3$ are as defined in claim 1, Z is an acid labile group having an oxygen atom attached thereto or $R^2O$— or $(R^2)_2N$—, g is an integer of 0 to 4, h is an integer of 1 to 5, g+h=5, e is an integer of 1 to 3, f is an integer of 0 to 2, and e+f=3.

4. The sulfonium salt of claim 3 wherein the acid labile group is selected from the class consisting of tert-butoxy, tert-amyloxy, tert-butoxycarbonyloxy, tert-butoxycarbonyl-methyloxy, 1-ethoxyethoxy, tetrahydropyranyloxy, tetrahydrofuranyloxy, trimethylsilyloxy, and 1-ethylcyclopentyloxy groups.

5. A iodonium salt of the following formula (1b):

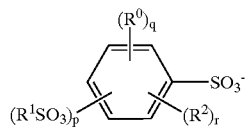
(1b)

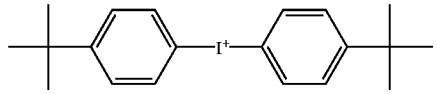

wherein $R^1$, $R^2$, $R^0$, p, q, and r are as defined in claim 1.

6. A photoacid generator for a chemical amplification type resist composition comprising the onium salt of claim 1.

7. A chemical amplification type resist composition comprising
(A) a resin which changes its solubility in an alkaline developer under the action of an acid, and
(B) the photoacid generator of claim 6 which generates an acid upon exposure to radiation.

8. A chemical amplification type resist composition comprising
(A) a resin which changes its solubility in an alkaline developer under the action of an acid,
(B) the photoacid generator of claim 6 which generates an acid upon exposure to radiation, and
(C) a compound capable of generating an acid upon exposure to radiation, other than component (B).

9. The resist composition of claim 7 wherein the resin (A) has such substituent groups having C—O—C linkages that the solubility in an alkaline developer changes as a result of scission of the C—O—C linkages under the action of an acid.

10. The resist composition of claim 7 further comprising (D) a basic compound.

11. The resist composition of claim 7 further comprising (E) a carboxyl group-containing compound.

12. A process for forming a pattern, comprising the steps of:
applying the resist composition of claim 7 onto a substrate to form a coating,
heat treating the coating and exposing the coating to high energy radiation with a wavelength of up to 300 nm or electron beam through a photo-mask,
optionally heat treating the exposed coating, and developing the coating with a developer.

* * * * *